(12) United States Patent  (10) Patent No.: US 8,317,677 B2
Bertolote et al.  (45) Date of Patent: Nov. 27, 2012

(54) MECHANICAL GASTRIC BAND WITH CUSHIONS

(75) Inventors: Tiago Bertolote, Geneva (CH); Pierre Fridez, Froideville (CH)

(73) Assignee: Allergan, Inc., Irvine, CA (US)

( * ) Notice: Subject to any disclaimer, the term of this patent is extended or adjusted under 35 U.S.C. 154(b) by 542 days.

(21) Appl. No.: 12/574,640

(22) Filed: Oct. 6, 2009

(65) Prior Publication Data

US 2010/0087843 A1  Apr. 8, 2010

Related U.S. Application Data

(60) Provisional application No. 61/103,153, filed on Oct. 6, 2008.

(51) Int. Cl.
 *A61F 2/00* (2006.01)
 *A61F 13/00* (2006.01)
 *A61B 17/08* (2006.01)
(52) U.S. Cl. ........................... 600/37; 606/157
(58) Field of Classification Search ................ 600/37; 606/157
 See application file for complete search history.

(56) References Cited

U.S. PATENT DOCUMENTS

| | | |
|---|---|---|
| 1,174,814 A | 3/1916 | Brennan et al. |
| 1,830,947 A | 11/1931 | Klingel |
| 1,999,683 A | 4/1935 | Borresen |
| 2,163,048 A | 6/1939 | McKee |
| 2,339,138 A | 1/1944 | Black |
| 2,405,667 A | 8/1946 | Ottesen |
| 2,438,231 A | 3/1948 | Schultz et al. |
| 2,635,907 A | 4/1953 | Heimbuch |
| 2,714,469 A | 8/1955 | Carlson |
| 2,936,980 A | 5/1960 | Rapata |
| 3,059,645 A | 10/1962 | Hasbrouck et al. |
| 3,189,961 A | 6/1965 | Heller |
| 3,667,081 A | 6/1972 | Burger |
| 3,840,018 A | 10/1974 | Heifetz |
| 3,955,834 A | 5/1976 | Ahlrot |
| 4,053,176 A | 10/1977 | Hilbush |
| 4,118,805 A | 10/1978 | Reimels |
| 4,133,315 A | 1/1979 | Berman et al. |
| 4,157,713 A | 6/1979 | Clarey |
| 4,176,412 A | 12/1979 | Peterson |
| 4,236,521 A | 12/1980 | Lauterjung |
| 4,271,827 A | 6/1981 | Angelchik |
| 4,299,012 A | 11/1981 | Oetiker |
| 4,340,083 A | 7/1982 | Cummins |

(Continued)

FOREIGN PATENT DOCUMENTS

CA  949965  6/1974

(Continued)

OTHER PUBLICATIONS

"Innovative medical devices and implants"; LGSP medical futures, p. 5.

(Continued)

*Primary Examiner* — Samuel Gilbert
*Assistant Examiner* — Sunita Reddy
(74) *Attorney, Agent, or Firm* — Stephen Donovan; Debra Condino

(57) ABSTRACT

A system for regulating the functioning of an organ or duct generally includes an implantable band structured to at least partially circumscribe an organ or duct and an actuating mechanism operable to effect constriction of the band. The system further includes a plurality of incompressible cushion segments defining a substantially star-shaped inner circumference of the band, the star-shape effective to prevent pinching and necrosis of tissue during adjustment.

21 Claims, 21 Drawing Sheets

U.S. PATENT DOCUMENTS

| | | |
|---|---|---|
| 4,399,809 A | 8/1983 | Baro et al. |
| 4,408,597 A | 10/1983 | Tenney, Jr. |
| 4,417,567 A | 11/1983 | Trick |
| 4,424,208 A | 1/1984 | Wallace et al. |
| 4,442,153 A | 4/1984 | Meltsch |
| 4,450,375 A | 5/1984 | Siegal |
| 4,485,805 A | 12/1984 | Foster, Jr. |
| 4,492,004 A | 1/1985 | Oetiker |
| 4,551,862 A | 11/1985 | Haber |
| 4,558,699 A | 12/1985 | Bashour |
| 4,559,699 A | 12/1985 | Owen et al. |
| 4,582,640 A | 4/1986 | Smestad et al. |
| 4,582,865 A | 4/1986 | Balazs et al. |
| 4,592,339 A | 6/1986 | Kuzmak et al. |
| 4,592,355 A | 6/1986 | Antebi |
| 4,601,713 A | 7/1986 | Fuqua |
| 4,671,351 A | 6/1987 | Rappe |
| 4,693,695 A | 9/1987 | Cheng |
| 4,694,827 A | 9/1987 | Weiner et al. |
| 4,696,288 A | 9/1987 | Kuzmak et al. |
| 4,708,140 A | 11/1987 | Baron |
| 4,716,154 A | 12/1987 | Malson et al. |
| 4,753,086 A | 6/1988 | Schmidt |
| 4,760,837 A | 8/1988 | Petit |
| 4,803,075 A | 2/1989 | Wallace et al. |
| 4,881,939 A | 11/1989 | Newman |
| 4,883,467 A | 11/1989 | Franetzki et al. |
| 4,886,787 A | 12/1989 | De Belder et al. |
| 4,896,787 A | 1/1990 | Delamour et al. |
| 4,915,690 A | 4/1990 | Cone et al. |
| 4,925,446 A | 5/1990 | Garay et al. |
| 4,944,659 A | 7/1990 | Labbe et al. |
| 4,958,791 A | 9/1990 | Nakamura |
| 4,969,899 A | 11/1990 | Cox, Jr. |
| 4,994,019 A | 2/1991 | Fernandez et al. |
| 5,045,060 A | 9/1991 | Melsky et al. |
| 5,074,868 A | 12/1991 | Kuzmak |
| 5,084,061 A | 1/1992 | Gau et al. |
| 5,089,019 A | 2/1992 | Grandjean |
| 5,091,171 A | 2/1992 | Yu et al. |
| 5,120,313 A | 6/1992 | Elftman |
| 5,143,724 A | 9/1992 | Leshchiner et al. |
| 5,152,770 A | 10/1992 | Bengmark et al. |
| 5,160,338 A | 11/1992 | Vincent |
| 5,188,609 A | 2/1993 | Bayless et al. |
| 5,224,494 A | 7/1993 | Enhorning |
| 5,226,429 A | 7/1993 | Kuzmak |
| 5,246,456 A | 9/1993 | Wilkinson |
| 5,246,698 A | 9/1993 | Leshchiner et al. |
| 5,259,399 A | 11/1993 | Brown |
| 5,326,349 A | 7/1994 | Baraff |
| 5,343,894 A | 9/1994 | Frisch et al. |
| 5,356,883 A | 10/1994 | Kuo et al. |
| 5,360,445 A | 11/1994 | Goldowsky |
| 5,391,156 A | 2/1995 | Hildwein et al. |
| 5,399,351 A | 3/1995 | Leshchiner et al. |
| 5,449,363 A | 9/1995 | Brust et al. |
| 5,449,368 A | 9/1995 | Kuzmak |
| 5,458,568 A | 10/1995 | Racchini et al. |
| 5,496,312 A | 3/1996 | Klicek |
| 5,509,888 A | 4/1996 | Miller |
| 5,531,716 A | 7/1996 | Luzio et al. |
| 5,535,752 A | 7/1996 | Halperin et al. |
| 5,554,113 A | 9/1996 | Novak et al. |
| 5,562,714 A | 10/1996 | Grevious |
| 5,601,604 A | 2/1997 | Vincent |
| 5,607,418 A | 3/1997 | Arzbaecher |
| 5,633,001 A | 5/1997 | Agerup |
| 5,653,718 A | 8/1997 | Yoon |
| 5,658,298 A | 8/1997 | Vincent et al. |
| 5,676,162 A | 10/1997 | Larson, Jr. et al. |
| 5,695,504 A | 12/1997 | Gifford, III et al. |
| 5,704,893 A | 1/1998 | Timm |
| 5,713,911 A | 2/1998 | Racenet et al. |
| 5,733,257 A | 3/1998 | Sternby |
| 5,748,200 A | 5/1998 | Funahashi |
| 5,759,015 A | 6/1998 | Van Lintel et al. |
| 5,766,232 A | 6/1998 | Grevious et al. |
| 5,769,877 A | 6/1998 | Barreras, Sr. |
| 5,785,295 A | 7/1998 | Tsai |
| 5,817,113 A | 10/1998 | Gifford, III et al. |
| 5,827,529 A | 10/1998 | Ono et al. |
| 5,833,698 A | 11/1998 | Hinchliffe et al. |
| 5,861,014 A | 1/1999 | Familoni |
| RE36,176 E | 3/1999 | Kuzmak |
| 5,886,042 A | 3/1999 | Yu et al. |
| 5,904,697 A | 5/1999 | Gifford, III et al. |
| 5,910,149 A | 6/1999 | Kuzmak |
| 5,928,195 A | 7/1999 | Malamud et al. |
| 5,938,669 A | 8/1999 | Klaiber et al. |
| 5,944,696 A | 8/1999 | Bayless et al. |
| 5,944,751 A | 8/1999 | Laub |
| 5,993,473 A | 11/1999 | Chan et al. |
| 6,013,679 A | 1/2000 | Kuo et al. |
| 6,024,340 A | 2/2000 | Lazarus et al. |
| 6,024,704 A | 2/2000 | Meador et al. |
| 6,042,345 A | 3/2000 | Bishop et al. |
| 6,048,309 A | 4/2000 | Flom et al. |
| 6,067,991 A | 5/2000 | Forsell |
| 6,074,341 A | 6/2000 | Anderson et al. |
| 6,074,378 A | 6/2000 | Mouri et al. |
| 6,083,249 A | 7/2000 | Familoni |
| 6,090,131 A | 7/2000 | Daley |
| 6,102,678 A | 8/2000 | Peclat |
| 6,102,922 A | 8/2000 | Jakobsson et al. |
| 6,164,933 A | 12/2000 | Tani et al. |
| 6,171,321 B1 | 1/2001 | Gifford, III et al. |
| 6,193,734 B1 | 2/2001 | Bolduc et al. |
| 6,203,523 B1 | 3/2001 | Haller et al. |
| 6,210,345 B1 | 4/2001 | Van Brunt |
| 6,210,347 B1 | 4/2001 | Forsell |
| 6,221,024 B1 | 4/2001 | Miesel |
| 6,224,857 B1 | 5/2001 | Romeo et al. |
| 6,306,088 B1 | 10/2001 | Krausman et al. |
| 6,327,503 B1 | 12/2001 | Familoni |
| 6,371,965 B2 | 4/2002 | Gifford, III et al. |
| 6,387,105 B1 | 5/2002 | Gifford, III et al. |
| 6,417,750 B1 | 7/2002 | Sohn |
| 6,419,696 B1 | 7/2002 | Ortiz et al. |
| 6,432,040 B1 | 8/2002 | Meah |
| 6,439,539 B1 | 8/2002 | Powell |
| 6,443,957 B1 | 9/2002 | Addis |
| 6,443,965 B1 | 9/2002 | Gifford, III et al. |
| 6,450,173 B1 | 9/2002 | Forsell |
| 6,450,946 B1 | 9/2002 | Forsell |
| 6,451,034 B1 | 9/2002 | Gifford, III et al. |
| 6,453,907 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,454,785 B2 | 9/2002 | De Hoyos Garza |
| 6,457,801 B1 | 10/2002 | Fish et al. |
| 6,460,543 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,474,584 B2 | 11/2002 | Ekich |
| 6,475,136 B1 | 11/2002 | Forsell |
| 6,485,496 B1 | 11/2002 | Suyker et al. |
| 6,491,704 B2 | 12/2002 | Gifford, III et al. |
| 6,491,705 B2 | 12/2002 | Gifford, III et al. |
| 6,511,490 B2 | 1/2003 | Robert |
| 6,517,556 B1 | 2/2003 | Monassevitch |
| 6,527,701 B1 | 3/2003 | Sayet et al. |
| 6,547,801 B1 | 4/2003 | Dargent et al. |
| 6,565,582 B2 | 5/2003 | Gifford, III et al. |
| 6,579,301 B1 | 6/2003 | Bales et al. |
| 6,601,604 B1 | 8/2003 | Cooper |
| 6,615,084 B1 | 9/2003 | Cigaina |
| 6,632,239 B2 | 10/2003 | Snyder et al. |
| 6,646,628 B2 | 11/2003 | Shirochi et al. |
| 6,676,674 B1 | 1/2004 | Dudai |
| 6,681,135 B1 | 1/2004 | Davis et al. |
| 6,685,668 B1 | 2/2004 | Cho et al. |
| 6,691,047 B1 | 2/2004 | Fredericks |
| 6,715,731 B1 | 4/2004 | Post et al. |

| Patent No. | Date | Name |
|---|---|---|
| 6,729,600 B2 | 5/2004 | Mattes et al. |
| 6,754,527 B2 | 6/2004 | Stroebel et al. |
| 6,811,136 B2 | 11/2004 | Eberhardt et al. |
| 6,820,651 B2 | 11/2004 | Seuret et al. |
| 6,834,201 B2 | 12/2004 | Gillies et al. |
| 6,871,090 B1 | 3/2005 | He et al. |
| 6,889,086 B2 | 5/2005 | Mass et al. |
| 6,916,326 B2 | 7/2005 | Benchetrit |
| 6,940,467 B2 | 9/2005 | Fischer et al. |
| 6,966,875 B1 | 11/2005 | Longobardi |
| 7,017,583 B2 | 3/2006 | Forsell |
| 7,017,883 B2 | 3/2006 | Bayer et al. |
| 7,021,147 B1 | 4/2006 | Subramanian et al. |
| 7,037,344 B2 | 5/2006 | Kagan et al. |
| 7,040,349 B2 | 5/2006 | Moler et al. |
| 7,048,519 B2 | 5/2006 | Fong et al. |
| 7,054,690 B2 | 5/2006 | Imran |
| 7,058,434 B2 | 6/2006 | Wang et al. |
| 7,060,080 B2 | 6/2006 | Bachmann |
| 7,066,486 B2 | 6/2006 | Lee |
| 7,118,526 B2 | 10/2006 | Egle |
| 7,119,062 B1 | 10/2006 | Alvis et al. |
| 7,128,750 B1 | 10/2006 | Stergiopulos |
| 7,144,400 B2 | 12/2006 | Byrum et al. |
| 7,172,607 B2 | 2/2007 | Hofle et al. |
| 7,177,693 B2 | 2/2007 | Starkebsum |
| 7,191,007 B2 | 3/2007 | Desai et al. |
| 7,198,250 B2 | 4/2007 | East |
| 7,204,821 B1 | 4/2007 | Clare et al. |
| 7,206,637 B2 | 4/2007 | Salo |
| 7,223,239 B2 | 5/2007 | Schulze et al. |
| 7,238,191 B2 | 7/2007 | Bachmann |
| 7,240,607 B2 | 7/2007 | Fish |
| 7,255,675 B2 | 8/2007 | Gertner et al. |
| 7,263,405 B2 | 8/2007 | Boveja et al. |
| 7,282,023 B2 | 10/2007 | Frering |
| 7,284,966 B2 | 10/2007 | Xu et al. |
| 7,288,064 B2 | 10/2007 | Boustani et al. |
| 7,297,103 B2 | 11/2007 | Jarsaillon et al. |
| 7,299,082 B2 | 11/2007 | Feldman et al. |
| 7,310,557 B2 | 12/2007 | Maschino et al. |
| 7,311,503 B2 | 12/2007 | Van Lintel et al. |
| 7,311,716 B2 | 12/2007 | Byrun |
| 7,311,717 B2 | 12/2007 | Egle |
| 7,314,443 B2 | 1/2008 | Jordan et al. |
| 7,314,636 B2 | 1/2008 | Caseres et al. |
| 7,338,433 B2 | 3/2008 | Coe |
| 7,340,306 B2 | 3/2008 | Barrett et al. |
| 7,351,198 B2 | 4/2008 | Byrum et al. |
| 7,351,240 B2 | 4/2008 | Hassler, Jr. et al. |
| 7,353,747 B2 | 4/2008 | Swayze et al. |
| 7,364,542 B2 | 4/2008 | Jambor et al. |
| 7,366,571 B2 | 4/2008 | Armstrong |
| 7,367,340 B2 | 5/2008 | Nelson et al. |
| 7,367,937 B2 | 5/2008 | Jambor et al. |
| 7,374,565 B2 | 5/2008 | Hassler, Jr. et al. |
| 7,390,294 B2 | 6/2008 | Hassler, Jr. |
| 7,396,353 B2 | 7/2008 | Lorenzen et al. |
| 7,416,528 B2 | 8/2008 | Crawford et al. |
| 7,457,668 B2 | 11/2008 | Cancel et al. |
| 7,481,763 B2 | 1/2009 | Hassler et al. |
| 7,500,944 B2 | 3/2009 | Byrum et al. |
| 7,502,649 B2 | 3/2009 | Ben-Haim et al. |
| 7,530,943 B2 | 5/2009 | Lechner |
| 7,594,885 B2 | 9/2009 | Byrum |
| 7,599,743 B2 | 10/2009 | Hassler, Jr. et al. |
| 7,599,744 B2 | 10/2009 | Giordano et al. |
| 7,601,162 B2 | 10/2009 | Hassler, Jr. et al. |
| 7,615,001 B2 | 11/2009 | Jambor et al. |
| 7,618,365 B2 | 11/2009 | Jambor et al. |
| 7,658,196 B2 | 2/2010 | Ferreri et al. |
| 7,670,279 B2 | 3/2010 | Gertner |
| 7,699,770 B2 | 4/2010 | Hassler, Jr. et al. |
| 7,712,470 B2 | 5/2010 | Gertner |
| 7,727,141 B2 | 6/2010 | Hassler, Jr. et al. |
| 7,741,476 B2 | 6/2010 | Lebreton |
| 7,758,493 B2 | 7/2010 | Gingras |
| 7,763,039 B2 | 7/2010 | Ortiz et al. |
| 7,766,815 B2 | 8/2010 | Ortiz |
| 7,771,439 B2 | 8/2010 | Griffiths |
| 7,775,215 B2 | 8/2010 | Hassler, Jr. et al. |
| 7,775,966 B2 | 8/2010 | Dlugos et al. |
| 7,775,967 B2 | 8/2010 | Gertner |
| 7,794,386 B2 | 9/2010 | Brooks |
| 7,811,298 B2 | 10/2010 | Birk |
| 7,828,813 B2 | 11/2010 | Mouton |
| 7,832,407 B2 | 11/2010 | Gertner |
| 7,841,978 B2 | 11/2010 | Gertner |
| 7,844,342 B2 | 11/2010 | Dlugos et al. |
| 7,862,502 B2 | 1/2011 | Pool et al. |
| 7,879,068 B2 | 2/2011 | Dlugos et al. |
| 7,951,067 B2 | 5/2011 | Byrum et al. |
| 2001/0011543 A1 | 8/2001 | Forsell |
| 2002/0072780 A1 | 6/2002 | Foley |
| 2002/0091395 A1 | 7/2002 | Gabbay |
| 2002/0095181 A1 | 7/2002 | Beyar |
| 2002/0098097 A1 | 7/2002 | Singh |
| 2002/0139208 A1 | 10/2002 | Yatskov |
| 2002/0183765 A1 | 12/2002 | Adams |
| 2002/0198548 A1 | 12/2002 | Robert |
| 2003/0014003 A1 | 1/2003 | Gertner |
| 2003/0019498 A1 | 1/2003 | Forsell |
| 2003/0045775 A1 | 3/2003 | Forsell |
| 2003/0045902 A1 | 3/2003 | Weadock |
| 2003/0055311 A1 | 3/2003 | Neukermans et al. |
| 2003/0060873 A1 | 3/2003 | Gertner et al. |
| 2003/0066536 A1 | 4/2003 | Forsell |
| 2003/0073880 A1 | 4/2003 | Polsky et al. |
| 2003/0093157 A1 | 5/2003 | Casares et al. |
| 2003/0100910 A1 | 5/2003 | Gifford, III et al. |
| 2003/0120288 A1 | 6/2003 | Benchetrit |
| 2003/0148995 A1 | 8/2003 | Piron et al. |
| 2003/0158564 A1 | 8/2003 | Benchetrit |
| 2003/0158569 A1 | 8/2003 | Wazne |
| 2003/0181890 A1 | 9/2003 | Schulze et al. |
| 2003/0181917 A1 | 9/2003 | Gertner |
| 2003/0191433 A1 | 10/2003 | Prentiss |
| 2003/0208212 A1 | 11/2003 | Cigaina |
| 2004/0000843 A1 | 1/2004 | East |
| 2004/0044332 A1 | 3/2004 | Stergiopulos |
| 2004/0049209 A1 | 3/2004 | Benchetrit |
| 2004/0059393 A1 | 3/2004 | Policker et al. |
| 2004/0068847 A1 | 4/2004 | Belisle et al. |
| 2004/0133219 A1 | 7/2004 | Forsell |
| 2004/0147816 A1 | 7/2004 | Policker et al. |
| 2004/0148034 A1 | 7/2004 | Kagan et al. |
| 2004/0153106 A1 | 8/2004 | Dudai |
| 2004/0162595 A1 | 8/2004 | Foley |
| 2004/0215159 A1 | 10/2004 | Forsell |
| 2004/0230137 A1 | 11/2004 | Mouton |
| 2004/0254536 A1 | 12/2004 | Conlon et al. |
| 2004/0254537 A1 | 12/2004 | Conlon et al. |
| 2004/0260319 A1 | 12/2004 | Egle |
| 2004/0267288 A1 | 12/2004 | Byrum et al. |
| 2004/0267291 A1 | 12/2004 | Byrum et al. |
| 2004/0267292 A1 | 12/2004 | Byrum et al. |
| 2004/0267293 A1 | 12/2004 | Byrum et al. |
| 2004/0267377 A1 | 12/2004 | Egle |
| 2005/0002984 A1 | 1/2005 | Byrum et al. |
| 2005/0038484 A1 | 2/2005 | Knudson et al. |
| 2005/0038498 A1 | 2/2005 | Dubrow et al. |
| 2005/0055039 A1 | 3/2005 | Burnett et al. |
| 2005/0070934 A1 | 3/2005 | Tanaka et al. |
| 2005/0070937 A1 | 3/2005 | Jambor et al. |
| 2005/0100779 A1 | 5/2005 | Gertner |
| 2005/0104457 A1 | 5/2005 | Jordan et al. |
| 2005/0119672 A1 | 6/2005 | Benchetrit |
| 2005/0119674 A1 | 6/2005 | Gingras |
| 2005/0131383 A1 | 6/2005 | Chen et al. |
| 2005/0131485 A1 | 6/2005 | Knudson et al. |
| 2005/0136122 A1 | 6/2005 | Sadozai et al. |
| 2005/0142152 A1 | 6/2005 | Leshchiner et al. |
| 2005/0143765 A1 | 6/2005 | Bachmann et al. |
| 2005/0143766 A1 | 6/2005 | Bachmann et al. |
| 2005/0154274 A1 | 7/2005 | Jarsaillon et al. |
| 2005/0171568 A1 | 8/2005 | Duffy |
| 2005/0183730 A1 | 8/2005 | Byrum |
| 2005/0192531 A1 | 9/2005 | Birk |

| | | |
|---|---|---|
| 2005/0192601 A1 | 9/2005 | Demarais |
| 2005/0192629 A1 | 9/2005 | Saadat et al. |
| 2005/0216042 A1 | 9/2005 | Gertner |
| 2005/0226936 A1 | 10/2005 | Agerup |
| 2005/0228415 A1 | 10/2005 | Gertner |
| 2005/0228504 A1 | 10/2005 | Demarais |
| 2005/0240155 A1 | 10/2005 | Conlon |
| 2005/0240156 A1 | 10/2005 | Conlon |
| 2005/0240279 A1 | 10/2005 | Kagan et al. |
| 2005/0244288 A1 | 11/2005 | O'Neill |
| 2005/0250979 A1 | 11/2005 | Coe |
| 2005/0251181 A1 | 11/2005 | Bachmann |
| 2005/0251182 A1 | 11/2005 | Bachmann |
| 2005/0267406 A1 | 12/2005 | Hassler, Jr. |
| 2005/0267500 A1 | 12/2005 | Hassler, Jr. |
| 2005/0267533 A1 | 12/2005 | Gertner |
| 2005/0271729 A1 | 12/2005 | Wang |
| 2005/0277899 A1 | 12/2005 | Conlon et al. |
| 2005/0283041 A1 | 12/2005 | Egle |
| 2005/0288739 A1 | 12/2005 | Hassler, Jr. et al. |
| 2005/0288740 A1 | 12/2005 | Hassler, Jr. et al. |
| 2006/0015138 A1 | 1/2006 | Gertner |
| 2006/0020298 A1 | 1/2006 | Camilleri et al. |
| 2006/0041183 A1 | 2/2006 | Massen et al. |
| 2006/0074439 A1 | 4/2006 | Garner et al. |
| 2006/0074473 A1 | 4/2006 | Gertner |
| 2006/0089571 A1 | 4/2006 | Gertner |
| 2006/0122147 A1 | 6/2006 | Wohlrab |
| 2006/0142700 A1 | 6/2006 | Sobelman et al. |
| 2006/0142790 A1 | 6/2006 | Gertner |
| 2006/0161186 A1 | 7/2006 | Hassler, Jr. et al. |
| 2006/0167531 A1 | 7/2006 | Gertner et al. |
| 2006/0173238 A1 | 8/2006 | Starkebaum |
| 2006/0173424 A1 | 8/2006 | Conlon |
| 2006/0178555 A1 | 8/2006 | Bortolotti |
| 2006/0183967 A1 | 8/2006 | Lechner |
| 2006/0189887 A1 | 8/2006 | Hassler, Jr. et al. |
| 2006/0189888 A1 | 8/2006 | Hassler, Jr. et al. |
| 2006/0189889 A1 | 8/2006 | Gertner |
| 2006/0194758 A1 | 8/2006 | Lebreton |
| 2006/0195139 A1 | 8/2006 | Gertner |
| 2006/0197412 A1 | 9/2006 | Rasmussen |
| 2006/0199997 A1 | 9/2006 | Hassler, Jr. et al. |
| 2006/0211912 A1 | 9/2006 | Dlugos et al. |
| 2006/0211913 A1 | 9/2006 | Dlugos et al. |
| 2006/0211914 A1 | 9/2006 | Hassler, Jr. et al. |
| 2006/0212051 A1 | 9/2006 | Snyder et al. |
| 2006/0212053 A1 | 9/2006 | Gertner |
| 2006/0235448 A1 | 10/2006 | Roslin et al. |
| 2006/0246137 A1 | 11/2006 | Hermitte et al. |
| 2006/0247721 A1 | 11/2006 | Maschino et al. |
| 2006/0247722 A1 | 11/2006 | Maschino et al. |
| 2006/0252982 A1 | 11/2006 | Hassler, Jr. et al. |
| 2006/0252983 A1 | 11/2006 | Lembo et al. |
| 2006/0257488 A1 | 11/2006 | Hubbard |
| 2006/0264699 A1 | 11/2006 | Gertner |
| 2006/0276812 A1 | 12/2006 | Hill et al. |
| 2006/0293627 A1 | 12/2006 | Byrum et al. |
| 2007/0015954 A1 | 1/2007 | Dlugos |
| 2007/0015955 A1 | 1/2007 | Tsonton |
| 2007/0015956 A1 | 1/2007 | Crawford et al. |
| 2007/0016231 A1 | 1/2007 | Jambor et al. |
| 2007/0016262 A1 | 1/2007 | Gross et al. |
| 2007/0027356 A1 | 2/2007 | Ortiz |
| 2007/0027358 A1 | 2/2007 | Gertner et al. |
| 2007/0044655 A1 | 3/2007 | Fish |
| 2007/0077292 A1 | 4/2007 | Pinsky |
| 2007/0078476 A1 | 4/2007 | Hull, Sr. et al. |
| 2007/0125826 A1 | 6/2007 | Shelton |
| 2007/0156013 A1 | 7/2007 | Birk |
| 2007/0167672 A1 | 7/2007 | Dlugos et al. |
| 2007/0167982 A1 | 7/2007 | Gertner et al. |
| 2007/0173685 A1 | 7/2007 | Jambor et al. |
| 2007/0173888 A1 | 7/2007 | Gertner et al. |
| 2007/0179335 A1 | 8/2007 | Gertner et al. |
| 2007/0185373 A1 | 8/2007 | Tsonton |
| 2007/0185462 A1 | 8/2007 | Byrum |
| 2007/0213836 A1 | 9/2007 | Paganon |
| 2007/0218083 A1 | 9/2007 | Brooks |
| 2007/0232848 A1 | 10/2007 | Forsell |
| 2007/0232849 A1 | 10/2007 | Gertner |
| 2007/0233170 A1 | 10/2007 | Gertner |
| 2007/0235083 A1 | 10/2007 | Dlugos |
| 2007/0243227 A1 | 10/2007 | Gertner |
| 2007/0250085 A1 | 10/2007 | Bachmann et al. |
| 2007/0250086 A1 | 10/2007 | Wiley et al. |
| 2007/0255335 A1 | 11/2007 | Herbert et al. |
| 2007/0255336 A1 | 11/2007 | Herbert et al. |
| 2007/0265598 A1 | 11/2007 | Karasik |
| 2007/0265645 A1 | 11/2007 | Birk et al. |
| 2007/0265646 A1 | 11/2007 | McCoy et al. |
| 2007/0298005 A1 | 12/2007 | Thibault |
| 2008/0009680 A1 | 1/2008 | Hassler, Jr. |
| 2008/0015406 A1 | 1/2008 | Dlugos et al. |
| 2008/0015501 A1 | 1/2008 | Gertner |
| 2008/0027269 A1 | 1/2008 | Gertner |
| 2008/0027469 A1 | 1/2008 | Bachmann |
| 2008/0071306 A1 | 3/2008 | Gertner |
| 2008/0097496 A1 | 4/2008 | Chang et al. |
| 2008/0108862 A1 | 5/2008 | Jordan et al. |
| 2008/0147002 A1 | 6/2008 | Gertner |
| 2008/0161717 A1 | 7/2008 | Gertner |
| 2008/0161875 A1 | 7/2008 | Stone |
| 2008/0166028 A1 | 7/2008 | Turek et al. |
| 2008/0167647 A1 | 7/2008 | Gertner |
| 2008/0167648 A1 | 7/2008 | Gertner |
| 2008/0172072 A1 | 7/2008 | Pool et al. |
| 2008/0188766 A1 | 8/2008 | Gertner |
| 2008/0195092 A1 | 8/2008 | Kim et al. |
| 2008/0208240 A1 | 8/2008 | Paz |
| 2008/0221598 A1 | 9/2008 | Dlugos et al. |
| 2008/0243071 A1 | 10/2008 | Quijano et al. |
| 2008/0249806 A1 | 10/2008 | Dlugos et al. |
| 2008/0250340 A1 | 10/2008 | Dlugos et al. |
| 2008/0250341 A1 | 10/2008 | Dlugos et al. |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0275294 A1 | 11/2008 | Gertner |
| 2008/0275295 A1 | 11/2008 | Gertner |
| 2008/0275484 A1 | 11/2008 | Gertner |
| 2008/0281347 A1 | 11/2008 | Gertner |
| 2008/0287969 A1 | 11/2008 | Tsonton et al. |
| 2008/0287974 A1 | 11/2008 | Widenhouse et al. |
| 2008/0287976 A1 | 11/2008 | Weaner et al. |
| 2008/0300618 A1 | 12/2008 | Gertner |
| 2008/0319435 A1 | 12/2008 | Rioux et al. |
| 2009/0054914 A1 | 2/2009 | Lechner |
| 2009/0062825 A1 | 3/2009 | Pool et al. |
| 2009/0062826 A1 | 3/2009 | Steffen |
| 2009/0082793 A1 | 3/2009 | Birk |
| 2009/0118572 A1 | 5/2009 | Lechner |
| 2009/0149874 A1 | 6/2009 | Ortiz et al. |
| 2009/0157106 A1 | 6/2009 | Marcotte et al. |
| 2009/0157107 A1 | 6/2009 | Kierath et al. |
| 2009/0157113 A1 | 6/2009 | Marcotte et al. |
| 2009/0171375 A1 | 7/2009 | Coe et al. |
| 2009/0171378 A1 | 7/2009 | Coe et al. |
| 2009/0171379 A1 | 7/2009 | Coe et al. |
| 2009/0187202 A1 | 7/2009 | Ortiz et al. |
| 2009/0192404 A1 | 7/2009 | Ortiz et al. |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1 | 8/2009 | Ortiz et al. |
| 2009/0204132 A1 | 8/2009 | Ortiz et al. |
| 2009/0204141 A1 | 8/2009 | Dlugos, Jr. et al. |
| 2009/0204179 A1 | 8/2009 | Dlugos, Jr. et al. |
| 2009/0209995 A1 | 8/2009 | Byrum et al. |
| 2009/0216255 A1 | 8/2009 | Coe et al. |
| 2009/0220176 A1 | 9/2009 | Fusco |
| 2009/0222031 A1 | 9/2009 | Axelsson |
| 2009/0222065 A1 | 9/2009 | Dlugos, Jr. et al. |

| | | | |
|---|---|---|---|
| 2009/0228063 A1 | 9/2009 | Dlugos, Jr. et al. | |
| 2009/0228072 A1 | 9/2009 | Coe et al. | |
| 2009/0270904 A1 | 10/2009 | Birk et al. | |
| 2009/0306462 A1 | 12/2009 | Lechner | |
| 2009/0312785 A1 | 12/2009 | Stone et al. | |
| 2010/0010291 A1 | 1/2010 | Birk et al. | |
| 2010/0087843 A1 | 4/2010 | Bertolote et al. | |
| 2010/0099945 A1 | 4/2010 | Birk et al. | |
| 2010/0100079 A1 | 4/2010 | Berkcan | |
| 2010/0145378 A1 | 6/2010 | Gertner | |
| 2010/0152532 A1 | 6/2010 | Marcotte | |
| 2010/0168508 A1 | 7/2010 | Gertner | |
| 2010/0185049 A1 | 7/2010 | Birk et al. | |
| 2010/0191265 A1 | 7/2010 | Lau et al. | |
| 2010/0191271 A1 | 7/2010 | Lau et al. | |
| 2010/0204647 A1 | 8/2010 | Gertner | |
| 2010/0204723 A1 | 8/2010 | Gertner | |
| 2010/0226988 A1 | 9/2010 | Lebreton | |
| 2010/0228080 A1 | 9/2010 | Tavori et al. | |
| 2010/0234682 A1 | 9/2010 | Gertner | |
| 2010/0249803 A1 | 9/2010 | Griffiths | |
| 2010/0280310 A1 | 11/2010 | Raven | |
| 2010/0305397 A1 | 12/2010 | Birk et al. | |
| 2010/0312147 A1 | 12/2010 | Gertner | |
| 2010/0324358 A1 | 12/2010 | Birk et al. | |
| 2010/0324359 A1 | 12/2010 | Birk | |
| 2011/0201874 A1 | 8/2011 | Birk et al. | |

FOREIGN PATENT DOCUMENTS

| | | |
|---|---|---|
| CN | 1250382 | 4/2000 |
| CN | 1367670 | 9/2002 |
| DE | 4225524 | 2/1994 |
| DE | 10020688 | 12/2000 |
| EP | 0119596 | 9/1984 |
| EP | 0230747 | 8/1987 |
| EP | 0416250 | 3/1991 |
| EP | 0611561 | 8/1994 |
| EP | 0695558 | 2/1996 |
| EP | 0876808 | 11/1998 |
| EP | 1036545 | 9/2000 |
| EP | 1072282 | 1/2001 |
| EP | 1105073 | 6/2001 |
| EP | 1396242 | 3/2004 |
| EP | 1396243 | 3/2004 |
| EP | 1491167 | 12/2004 |
| EP | 1491168 | 12/2004 |
| EP | 1529502 | 5/2005 |
| EP | 1574189 | 9/2005 |
| EP | 1600183 | 11/2005 |
| EP | 1602346 | 12/2005 |
| EP | 1704833 | 9/2006 |
| EP | 1719480 | 11/2006 |
| EP | 1754890 | 11/2006 |
| EP | 1736123 | 12/2006 |
| EP | 1736195 | 12/2006 |
| EP | 1736202 | 12/2006 |
| EP | 1743605 | 1/2007 |
| EP | 1829504 | 9/2007 |
| EP | 1829505 | 9/2007 |
| EP | 1829506 | 9/2007 |
| EP | 1967168 | 9/2008 |
| EP | 1992315 | 11/2008 |
| EP | 2074970 | 7/2009 |
| EP | 2074971 | 7/2009 |
| EP | 1 547 549 B1 | 8/2009 |
| EP | 2087862 | 8/2009 |
| EP | 2095796 | 9/2009 |
| EP | 2095798 | 9/2009 |
| FR | 1566202 | 5/1969 |
| FR | 2688693 | 9/1993 |
| FR | 2769491 | 4/1999 |
| FR | 2783153 | 3/2000 |
| FR | 2797181 | 2/2001 |
| FR | 2799118 | 4/2001 |
| FR | 2823663 | 10/2002 |
| FR | 2855744 | 12/2004 |
| FR | 2921822 | 4/2009 |
| GB | 1174814 | 12/1969 |
| GB | 2090747 | 7/1982 |
| JP | 57-171676 | 10/1982 |
| JP | 1-67309 | 4/1989 |
| JP | 2-019147 | 1/1990 |
| JP | 2-132104 | 11/1990 |
| JP | 3-105702 | 11/1991 |
| JP | 11-244395 | 9/1999 |
| JP | 2003-526410 | 9/2003 |
| JP | 2005-131380 | 5/2005 |
| JP | 2005-334658 | 12/2005 |
| SE | 8503144 | 12/1986 |
| WO | WO 86/00079 | 1/1986 |
| WO | WO 86/00912 | 2/1986 |
| WO | WO 89/11701 | 11/1989 |
| WO | WO 90/00369 | 1/1990 |
| WO | WO 92/20349 | 11/1992 |
| WO | WO 94/02517 | 2/1994 |
| WO | WO 96/33751 | 1/1996 |
| WO | WO 98/35639 | 8/1998 |
| WO | WO 98/35640 | 8/1998 |
| WO | WO 00/00108 | 1/2000 |
| WO | WO 00/01428 | 1/2000 |
| WO | WO00/09047 A1 | 2/2000 |
| WO | WO 00/09048 | 2/2000 |
| WO | WO 00/15158 | 3/2000 |
| WO | WO 00/66196 | 11/2000 |
| WO | WO 01/10359 | 2/2001 |
| WO | WO 01/12078 | 2/2001 |
| WO | WO 01/41671 | 6/2001 |
| WO | WO 01/47435 | 7/2001 |
| WO | WO 01/47575 | 7/2001 |
| WO | WO 01/49245 | 7/2001 |
| WO | WO 01/52777 | 7/2001 |
| WO | WO 01/68007 | 9/2001 |
| WO | WO 01/70131 | 9/2001 |
| WO | WO 01/85071 | 11/2001 |
| WO | WO 02/05753 | 1/2002 |
| WO | WO 02/09792 | 2/2002 |
| WO | WO 02/19953 | 3/2002 |
| WO | WO 02/26317 | 4/2002 |
| WO | WO 02/053093 | 7/2002 |
| WO | WO 02/065948 | 8/2002 |
| WO | WO 02/096326 | 12/2002 |
| WO | WO 03/007782 | 1/2003 |
| WO | WO 03/055420 | 7/2003 |
| WO | WO 03/057092 | 7/2003 |
| WO | WO 03/059215 | 7/2003 |
| WO | WO 03/077191 | 9/2003 |
| WO | WO 03/101352 | 12/2003 |
| WO | WO 03/105732 | 12/2003 |
| WO | WO 2004/014245 | 2/2004 |
| WO | WO 2004/019671 A2 | 3/2004 |
| WO | WO 2004/108025 | 12/2004 |
| WO | WO 2004/112563 | 12/2004 |
| WO | WO 2005/007232 | 1/2005 |
| WO | WO 2005/009305 | 2/2005 |
| WO | WO 2005/067994 | 5/2005 |
| WO | WO 2005/072195 | 8/2005 |
| WO | WO 2005/087147 | 9/2005 |
| WO | WO 2005/094447 | 10/2005 |
| WO | WO 2005/112888 | 12/2005 |
| WO | WO 2006/049725 | 5/2006 |
| WO | WO 2006/083885 | 8/2006 |
| WO | WO 2006/108203 | 10/2006 |
| WO | WO 2007/067206 | 6/2007 |
| WO | WO 2007/081304 | 7/2007 |
| WO | WO 2007/106727 | 9/2007 |
| WO | WO 2007/114905 | 10/2007 |
| WO | WO 2007/145638 | 12/2007 |
| WO | WO 2008/063673 | 5/2008 |
| WO | WO 2008/109300 | 9/2008 |
| WO | WO 2008/134755 | 11/2008 |
| WO | WO 2009/050709 | 4/2009 |
| WO | WO 2009/132127 | 10/2009 |
| WO | WO 2009/136126 | 11/2009 |
| WO | WO 2010/042493 | 4/2010 |

OTHER PUBLICATIONS

Acuna-Goycolea et al.; "Mechanism of Neuropeptide Y, Peptide YY, and Pancreatic Polypeptide Inhibition of Identified Green Fluorescent Protein-Expressing GABA Neurons in the Hypothalamic Neuroendocrine Acruate Nucleus"; The Journal of Neuroscience; V. 25(32); pp. 7406-7419; Aug. 10, 2005.
Adrian et al.; "Mechanism of Pancreatic Polypeptide Release in Man." The Lancet; pp. 161-163; Jan. 22, 1977.
Anson; "Shape Memory Alloys—Medical Applications," Source: Materials World, vol. 7, No. 12, pp. 745-747, Dec. 1999.
Asakawa et al; "Antagonism of Ghrelin Receptor Reduces Food Intake and Body Weight Gain in Mice"; Gut.; V.52; pp. 947-952; 2003.
Baggio et al. "Biology of Incretins: GLP-1 and GIP"; Gastroenrology; V. 132; pp. 2131-2157; 2007.
Ballantyne; "Peptide YY(1-36) and Peptide YY(3-36): Part I. Distribution, Release, and Actions"; Obesity Surgery; V.16; pp. 651-658; 2006.
Ballantyne; "Peptide YY(1-36) and Peptide YY(3-36): Part II. Changes after Gastrointestinal Surgery and Bariatric Surgery"; Obesity Surgery; V.16; pp. 795-803; 2006.
Berne et al; "Physiology"; V. 5; pp. 55-57, 210, 428, 540, 554, 579, 584, 591; 2004.
BioEnterics Lap-Band Adjustable Gastric Banding System, Inamed Health, pub., pp. 1-115; Aug. 28, 2003.
Boulant et al.; "Cholecystokinin in Transient Lower Oesophageal Sphincter Relaxation Due to Gastric Distension in Humans"; Gut.; V. 40; pp. 575-581; 1997.
Bradjewin et al.; "Dose Ranging Study of the Effects of Cholecystokinin in Healthy Volunteers"; J. Psychiatr. Neurosci.; V. 16 (2); pp. 91-95; 1991.
Burdyga et al.; "Cholecystokinin Regulates Expression of Y2 Receptors in Vagal Afferent Neurons Serving the Stomach"; The Journal of Neuroscience; V. 28; No. 45; pp. 11583-11592; Nov. 5, 2008.
Chaptini et al.; "Neuroendocrine Regulation of Food Intake"; Current Opinion in Gastroenterology; V. 24; pp. 223-229; 2008.
Chaudhri; "Can Gut Hormones Control Appetite and Prevent Obesity?" Diabetes Care; V. 31; Supp 2; pp. S284-S289; Feb. 2008.
Cohen et al.; "Oxyntomodulin Suppresses Appetite and Reduces Food Intake in Humans"; J. Clin. Endocrinol. Metab.; V. 88; No. 10; pp. 4696-4701; 2003.
Corno et al.; "A new implantable device for telemetric control of pulmonary blood flow"; New ideas; received in revised form Jul. 12, 2002; 10 pages.
Corno et al.; "FlowWatchTM in clipped and in clipped position"; Interact Cardio Vase Thorac Surg 2002; 1:46-49; Copyright @ 2002 The European Association for Cardio-thoracic Surgery; 1 page.
Cummings et al.; "Plasma Ghrelin Levels After Diet-Induced Weight Loss or Gastric Bypass Surgery"; N. Engl J. Med; V. 346, No. 21; pp. 1623-1630; May 23, 2002.
Cummings; "Gastrointestinal Regulation of Foot Intake"; The Food Journal of Clinical Investigation; V. 117, N. 1; pp. 13-23; Jan. 2007.
Dakin et al.; "Oxyntomodulin Inhibits Food Intake in the Rat"; Endocrinology; V. 142; No. 10; pp. 4244-4250; 2001.
Dakin et al.; "Peripheral Oxyntomodulin Reduces Food Intake and Body Weight gain in Rats"; Endocrinology; V. 145; No. 6; pp. 2687-2695; Jun. 2004.
Davison; "Activation of Vagal-Gastric Mechanoreceptors by Cholecystokinin"; Proc. West. Pharmocol. Soc.; V. 29; pp. 363-366; 1986.
De Waele et al.; "Endoscopic Volume Adjustment of Intragastric Balloons for Intolerance"; Obesity Surgery; V. 11; pp. 223-224; 2001.
De Waele et al.; "Intragastric Balloons for Preoperative Weight Reduction"; Obesity Surgery; V. 58; pp. 58-60; 2001.
Desai et al.; "Molecular Weight of Heparin Using 13C Nuclear Magnetic Resonance Spectroscopy" Journal of Pharmaceutical Science, V. 84, I 2; 1995, Abstract only.
Doldi et al.; "Intragastric Balloon: Another Option for Treatment of Obesity and Morbid Obesity"; Hepato-Gastroenterology; V. 51, N. 55; pp. 294-307; Jan.-Feb. 2004.
Doldi et al.; "Treatment of Morbid Obesity with Intragastric Balloon in Association with Diet"; Obesity Surgery; V. 10, pp. 583-587; 2000.
Doldi et al; "Intragastric Balloon in Obese Patients"; Obesity Surgery; V. 10, 578-581; 2000.

Ekblad et al.; "Distribution of Pancreatic Peptide and Peptide-YY"; Peptides; V. 23; pp. 251-261; 2002.
El Khoury et al.; "Variation in Postprandial Ghrelin Status Following Ingestion of High-Carbohydrate, High Fat, and High Protein Meals in Males"; Ann Nutr Metab; V. 50; pp. 260-269; 2006.
Galloro et al; "Preliminary Endoscopic Technical Report of an New Silicone Intragastric Balloon in the Treatment of Morbid Obesity"; Obesity Surgery; V. 9, pp. 68-71; 1999.
GinShiCel MH Hydroxy Propyl Methyl Cellulose, Web Page http://www.ginshicel.cn/MHPC.html, Nov. 12, 2008.
Girard; "The incretins: From the concept to their use in the treatment of type 2 diabetes. Part A: Incretins: Concept and physiological functions"; Diabetes and Metabolism; V. 34; pp. 550-559; 2008.
Greenough et al.; "Untangling the Effects of Hunger, Anxiety, and Nausea on Energy Intake During Intravenous Cholecystokinin Octapeptide (CCK-8) Infusion"; Physiology & Behavior; V. 65, No. 2; pp. 303-310; 1998.
Grise et al.; "Peptide YY Inhibits Growth of Human Breast Cancer in Vitro and in Vivo"; Journal of Surgical Research; V. 82; pp. 151-155; 1999.
Grundy; "Signaling the State of the Digestive Tract"; Autonomic Neuroscience: Basic and Clinical; V. 125; pp. 76-80; 2006.
Grundy; "Vagal Control of Gastrointestinal Function"; Bailliere's Clinical Gastroenterology; V. 2; No. 1; pp. 23-43; 1988.
Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.
Hameed et al.; "Gut hormones and appetite control." Oral Diseases; V. 15; pp. 18-26; 2009.
Hassan et al.; "Effects of Adjuvants to Local Anesthetics on Their Duration III Experimental Studies of Hyaluronic Acid" Abstract Pub Med [Acta Anesthesiol Scand.; 29 (4): 384-8], 1 page; May 1985.
Hodson et al.; "Management of Obesity with the New Intragastric Balloon"; Obesity Surgery; V. 11, pp. 327-329, 2001.
Holzer; "Gastrointestinal Afferents as Targets of Novel Drugs for the Treatment of Functional Bowel Disorders and Visceral Pain"; European Journal of Pharmacology; V. 429; pp. 177-193; 2001.
Houpt; "Gastrointestinal Factors in Hunger and Satiety." Neuroscience and Behavioral Reviews; V. 6; pp. 145-164; 1982.
Iverson et al.; "Recent Advances in Microscale Pumping Technologies: A Review and Evaluation"; Microfluid Nanofluid; vol. 5; pp. 145-174; Feb. 19, 2008.
Jones; "Molecular, pharmacological, and clinical aspects of liraglutide, a oncedaily human GLP-1 analogue"; Molecular and Cellular Endocrinology; V. 297; pp. 137-140; 2009.
Kerem et al.; "Exogenous Ghrelin Enhances Endocrine and Exocrine Regeneration in Pancreatectomized Rats"; J. Gastrointest Surg.; V. 13; pp. 775-783, 2009.
Kesty et al.; "Hormone-based therapies in the regulation of fuel metabolism and body weight"; Expert Opin. Biol. Ther.; V. 8; No. 11; pp. 1733-1747; 2008.
Kissileff et al.; "Peptides that Regulate Food Intake: Cholecystokinin and Stomach Distension Combine to Reduce Food Intake in Humans"; Am. J. Physiol. Regul. Integr. Comp. Physiol; V. 285; pp. 992-998; 2003.
Kojima et al.; "A role for pancreatic polypeptide in feeding and body weight regulation." Peptides; V. 28; pp. 459-463; 2007.
Kulicke et al. "Visco-Elastic Propeerties of Sodium Hyaluronate Solutions," American Institute of Physics; pp. 585-587; 2008.
LAP-BAND AP System Adjustable Gastric Banding System with OmniformTM Design: Directions for Use (DFU); Allergan, 16 pages; 2009.
Le Roux et al.; "Gut Hormone Profiles Following Bariatric Surgery Favor an Anorectic State, Facilitate Weight Loss, and Improve Metabolic Parameters"; Ann. Surg; V. 243; No. 1; pp. 108-114; Jan. 2006.
Liu et al.; "Adjuvant Hormonal Treatment With Peptide YY or Its Analog Decreases Human Pancreatic Carcinoma Growth"; The American Journal of Surgery; V. 171; pp. 192-196; Jan. 1996.
Mathus-Vliegen et al. "Intragastric Balloons for Morbid Obesity: Results, Patient Tolerance and Balloon Life Span"; Br. J. Surg.; V. 77, No. 7, pp. 76-79; Jan. 1990.

Mathus-Vliegen et al. "Treating Morbid and Supermorbid Obesity" International Journal of Gastroenterology; V. 5, No. 1, pp. 9-12; 2000.

Medeiros et al.; "Processing and metabolism of Peptide-YY: Pivotal roles of Dipeptidase-IV, Aminopeptidase-P, and Endopeptidase-24.11"; Endocrinology; V. 134, No. 5; pp. 2088-2094; 1994.

Naslund et al. "Pranidal subcutaneous injections of glucagon-like peptide-1 cause weight loss in obese human subjects"; British Journal of Nutrition; V. 91; pp. 439-446; 2004.

Potier et al.; "Protein, amino acids, and the control of food intake"; Current Opinion in Clinical Nutrition and Metabolic Care; V. 12; pp. 54-58; 2009.

Qian et al.; "Pulmonary delivery of a GLP-1 receptor agonist, BMS-686117"; International Journal of Pharmaceutics; V. 366; pp. 218-220; 2008.

Rang et al.; "Pharmacology"; V. 5; pp. 203, 397, 402, 524; 2004.

Raybould et al.; "Integration of Postprandial Gastrointestinal Tract: Role of CCK and Sensory Pathways"; Annals of New York Academy of Science; pp. 143-156; 1994.

Renshaw et al. "Peptide YY: A Potential Therapy for Obesity"; Current Drug Targets; V. 6; pp. 171-179; 2005.

Sannino et al.; "Crosslinking of Cellulose Derivatives and Hyaluronic Acid with Water-Soluble Carbodiimide" Polymer 46; pp. 11206-11212; 2005.

Shechter et al.; "Reversible PEGylation of peptide YY3-36 prolongs its inhibition of food intake in mice"; FEBS Letters; V. 579; pp. 2439-2444; 2005.

Silver et al.; "Physical Properties of Hyaluronic Acid and Hydroxypropylmethylcellulose in Solution: Evaluation of Coating Ability" Journal of Applied Biomaterials, V. 5; pp. 89-98, 1994.

Small et al.; "Gut hormones and the control of appetite"; TRENDS in Endocrinology and Metabolism; V. 15; No. 6; pp. 259-263; Aug. 2004.

Stanley et al.; "Gastrointestinal Satiety Signals III. Glucagon-like Peptide 1, oxyntomodulin, peptide YY, and pancreatic polypeptide"; Am. J. Physiol Gastrointest Liver Physiol; V. 286; pp. 693-697; 2004.

Tezel; "The Science of Hyaluronic Acid Dermal Fillers," Journal of Cosmetic and Laser Therapy (2008) 10: pp. 35-42.

Tolhurst et al.; "Nutritional regulation of glucagon-like peptidel secretion"; J. Physiol.; V. 587, No. 1; pp. 27-32; 2009.

Totte et al.; "Weight Reduction by Means of Intragastric Device: Experience with the Bioenterics Intragastric Balloon"; Obesity Surgery; V. 11, pp. 519-523; 2001.

Tough et al.; "$Y_4$ Receptors Mediate the Inhibitory Responses of Pancreatic Polypeptide in Human and Mouse Colon Mucosa"; The Journal of Pharmacology and Experimental Therapeutics; V. 319, No. 1; pp. 20-30; 2006.

Tseng et al; "Peptide YY and cancer: Current findings and potential clinical applications"; Peptides; V. 23; pp. 389-395; 2002.

Valassi et al.; "Neuroendocrine control of food intake"; Nut. Metab. & Cariovasc. Disease; V. 18; pp. 158-168; 2008.

Van Der Lely et al.; "Biological, Physiological, Pathophysiological Aspects of Ghrelin"; Endocrine Reviews; V. 25, No. 3; pp. 426-457; 2004.

Verdich et al. "A Meta-Analysis of the Effect of Glucagon-Like-Peptide-1 (7-36) Amide on ad Libitum Energy Intake in Humans"; J. Clin. Endocrinal. Metab. V. 86; pp. 4382-4389; Sep. 2001.

Wahlen et al.; "The BioEnterics Intragastric Balloon (BIB): How to Use It"; Obesity Surgery; V. 11; pp. 524-527; 2001.

Wang et al.; "Plasma Ghrelin Modulation in Gastric Band Operation and Sleeve Gastrectomy"; Obes. Surg.; pp. 357-362; 2008.

Weiner et al.; "Preparation of Extremely Obese Patients for Laparoscopic Gastric Banding by Gastric Balloon Therapy"; Obesity Surgery; V. 9, pp. 261-264, 1999.

Wynne et al.; "Subcutaneous Oxyntomodulin Reduces Body Weight in Overweight and Obese Subjects: A Double-Blind Randomized, Controlled Trial"; Diabetes; V. 54; pp. 2390-2395; 2005.

Yuzuriha et al.; "Gastrointestinal Hormones (anorexigenic peptide YY and orexigenic ghrelin) influence neural tube development"; FASEB J.; V. 21; pp. 2108-2112; 2007.

Brown et al; "Symmetrical Pouch Dilation After Laparoscopic Adjustable Gastric Banding: Incidence and Management"; Obesity Surgery; V. 18, pp. 1104-1108; 2008.

Ceelen et al.; "Surgical Treatment of Severe Obesity With a Low-Pressure Adjustable Gastric Band: Experimental Data and Clinical Results in 625 Patients"; Annals of Surgery; V. 237, No. 1; pp. 10-16; 2003.

Dixon et al.; "Pregnancy After Lap-Band Surgery: Management of the Band to Achieve Healthy Weight Outcomes"; Obesity Surgery; V. 11, pp. 59-65; 2001.

Neary et al.; "Peptide YY(3-36) and Glucagon-Like Peptide-$1_{(7-36)}$ Inhibit Food Intake Additively"; Endocrinology; V.146; pp. 5120-5127; 2005.

Padidela et al.; "Elevated basal and post-feed glucagon-like petide 1 (GLP-1) concentrations in the neonatel period"; European Journal of Endocrinology; v. 160; pp. 53-58; 2009.

Shi et al.; "Sexually Dimorphic Responses to Fat Loss After Caloric Restriction or Surgical Lipectomy"; Am. J. Physiol. Endocrinol. Metab.; V. 293; E316-E326; 2007.

Xanthakos et al.; "Bariatric Surgery for Extreme Adolescent Obesity: Indications, Outcomes, and Physiologic Effects on the Gut-Brain Axis"; Pathophysiology; V. 15; pp. 135-146; 2008.

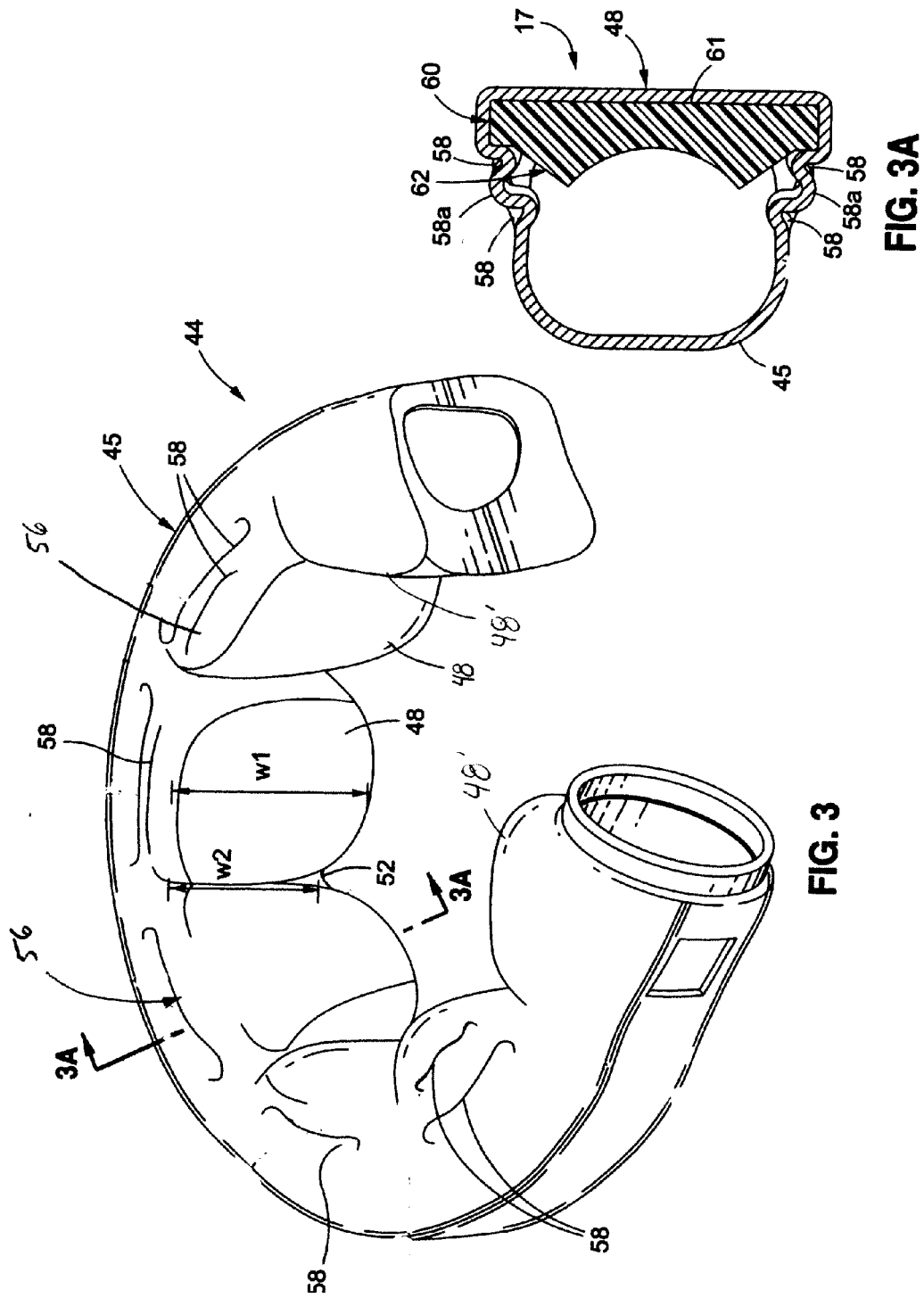

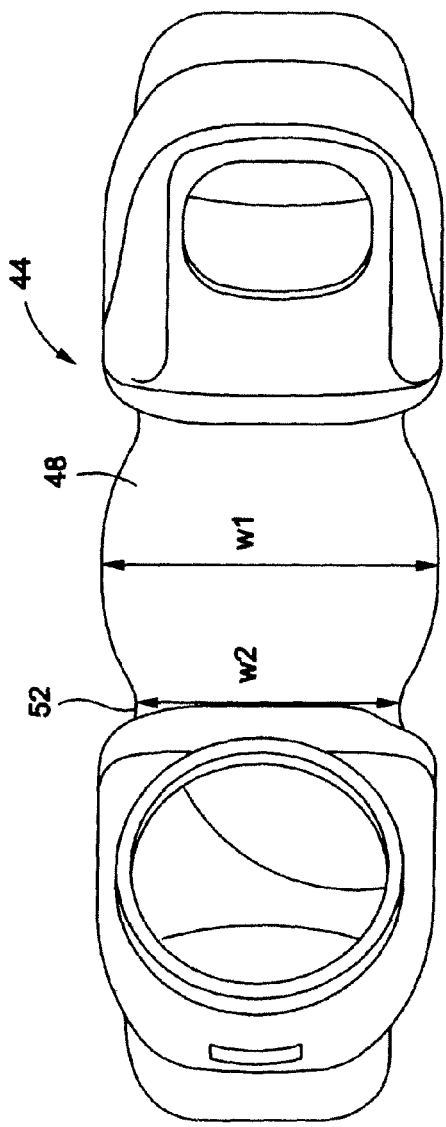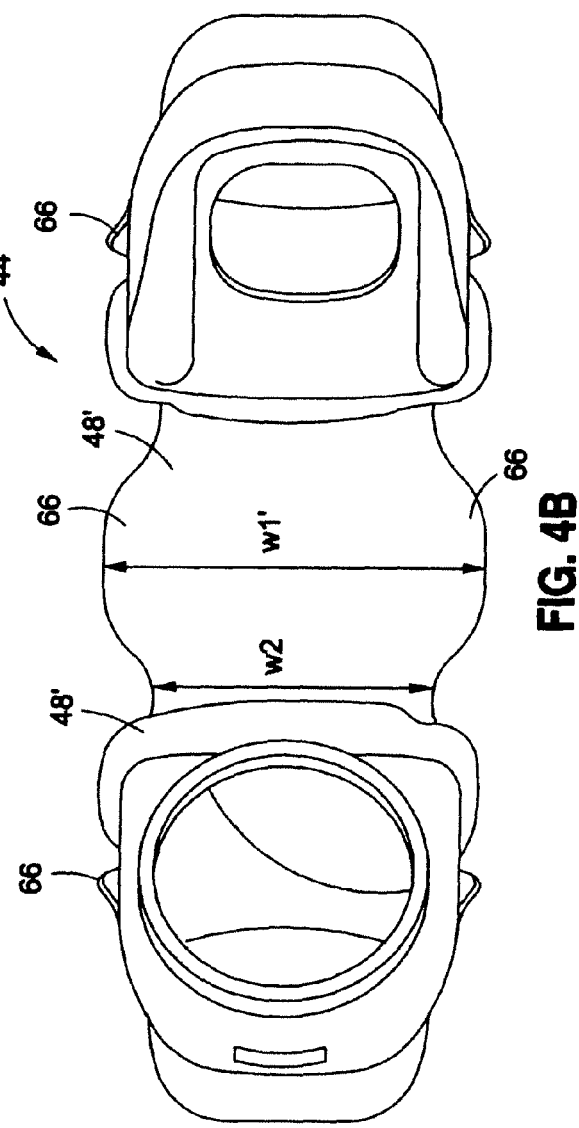

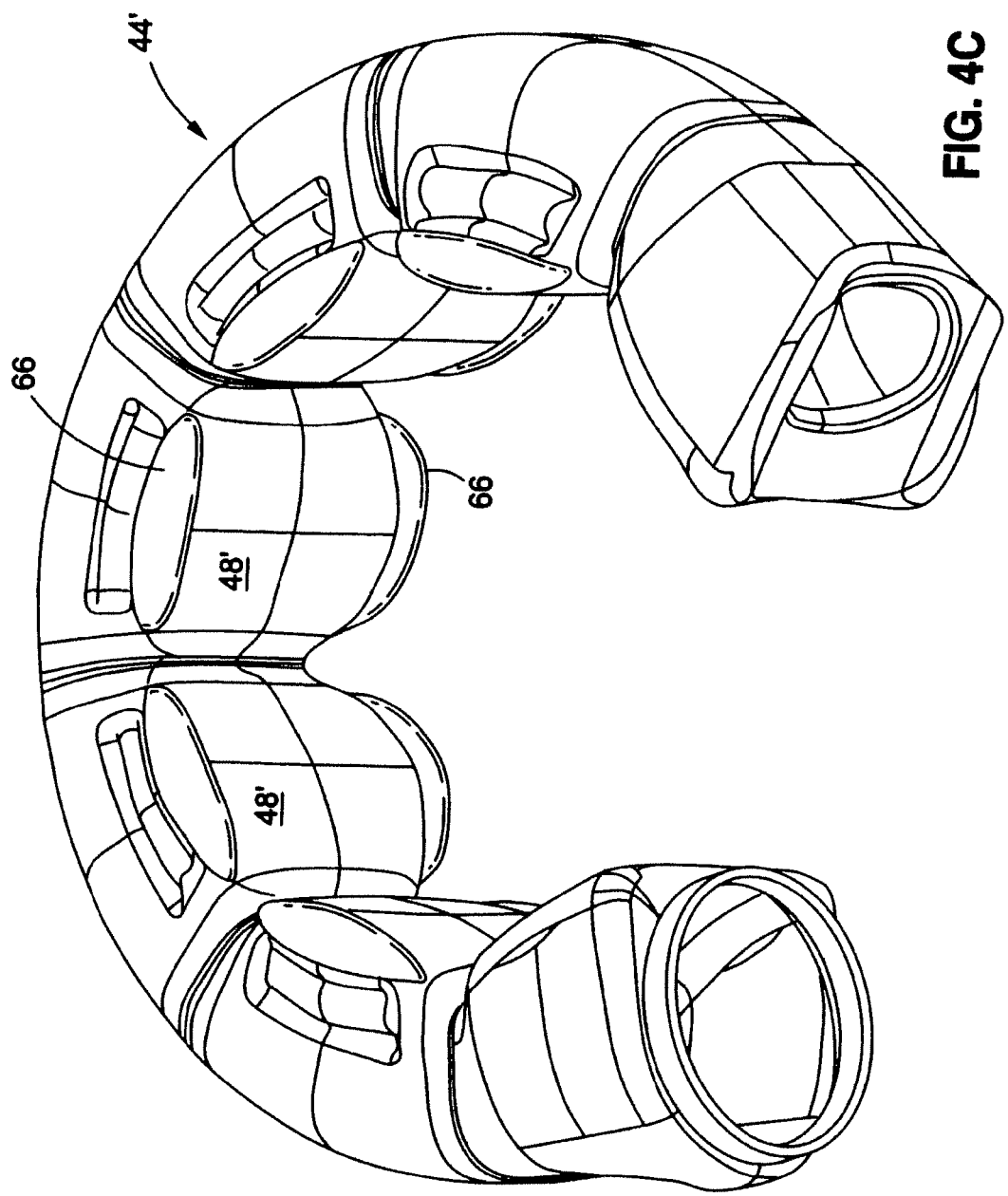

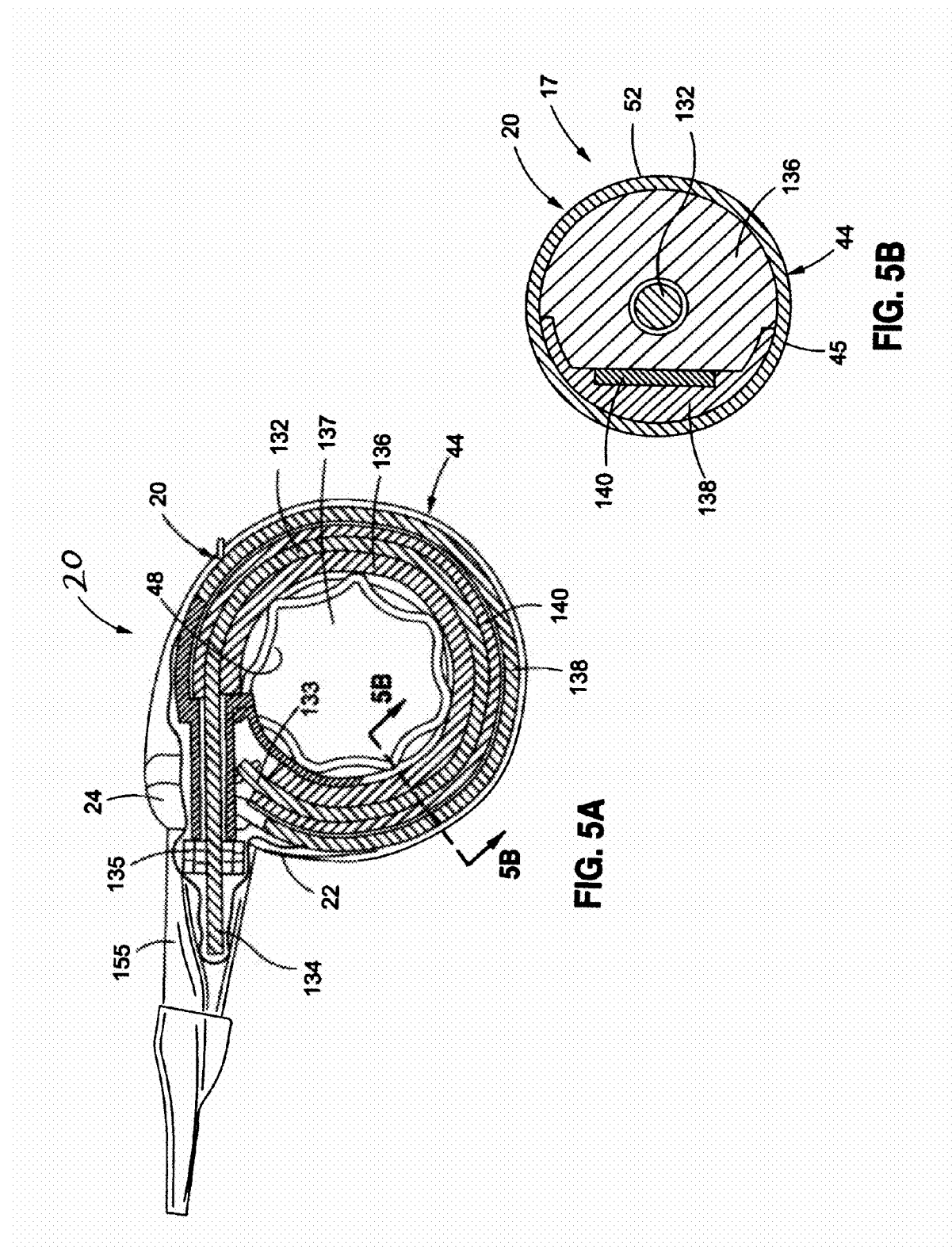

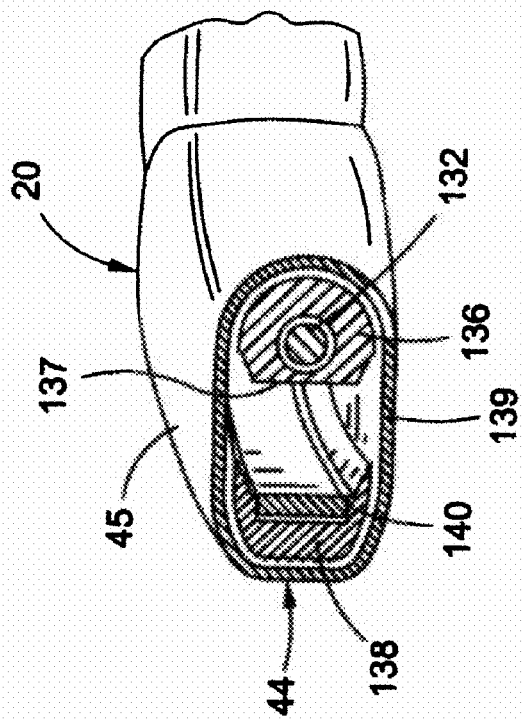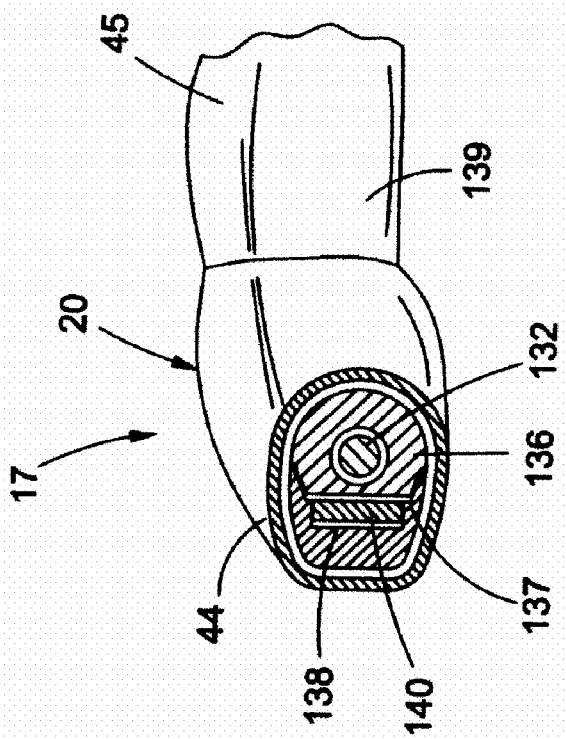
FIG. 5D
FIG. 5C

MECHANICAL GASTRIC BAND WITH CUSHIONS

RELATED APPLICATION

This application claims priority to and the benefit of U.S. Provisional Patent Application No. 61/103,153, filed on Oct. 6, 2008, the entire disclosure of which is incorporated herein by this reference.

BACKGROUND

This invention relates to surgical devices for regulating or controlling an organ or a duct, for example, a gastric banding system.

Obesity is well recognized as a serious health problem, and is associated with numerous health complications, ranging from non-fatal conditions to life threatening chronic diseases. According to the World Health Organization, debilitating health problems associated with obesity include respiratory difficulties, chronic musculoskeletal problems, skin problems and infertility. Life-threatening problems fall into four main areas: cardiovascular disease problems; conditions associated with insulin resistance such as type 2 diabetes; certain types of cancers, especially the hormonally related and large bowel cancers; and gallbladder disease. Beyond these physiological problems, obesity has also psychological consequences, ranging from lowered self-esteem to clinical depression.

Surgical intervention is sometimes indicated for people suffering from the effects of obesity. Such intervention not only mitigates the myriad health problems arising from being overweight, but may reduce the risk of early death of the patient. Left untreated, morbid obesity may reduce a patient's life expectancy by ten to fifteen years.

SUMMARY OF THE INVENTION

A system for regulating an organ or duct, for example, the functioning of an organ or duct, is provided. The system generally comprises an implantable band having a first end and a second end, a distal region and a proximal region, and a connector configured to couple the first end with the second end such that the band is formable into a loop configuration. The band is structured to circumscribe, or at least partially circumscribe, an organ or duct, for example, a stomach. The system further comprises a mechanism for enabling adjustment of an inner circumference of the loop configuration to effect constriction of the organ or duct.

For the sake of simplicity, and in no way intended to limit the scope of the invention, the "organ or duct" will hereinafter typically be referred to as a "stomach" and the system will be described as a gastric band system. The band is structured to circumscribe an upper portion of a stomach to form a stoma that controls the intake of food to the stomach. It is to be appreciated that although the invention is hereinafter typically described as pertaining to a gastric band system for application to a stomach, for example, for obesity treatment, the system, with appropriate modification thereto, can be used for regulating or controlling any organ or duct that would benefit from application of the present system thereto.

Once the band is implanted about the stomach, the size of an inner diameter of the band can be adjusted to provide the desired degree of restriction. Techniques for determining appropriate adjustment of gastric bands, timing and amount of adjustments, are known in the art and therefore will not be described in great detail herein.

Advantageously, in a broad aspect of the invention, the system may be structured to substantially prevent or at least reduce the occurrence of pinching of the body tissues, for example, the tissues of the stomach, during constriction or tightening of the band.

For example, in a specific embodiment, the system further comprises a contact region located between the first end and the second end of the band which is structured and functions to progressively move tissue, for example stomach tissue, during tightening of the band, without entrapping the tissue.

The contact region may comprise plurality of first segments and a plurality of second segments arranged in a generally alternating manner along the proximal (e.g. stomach-facing) region of the band. The first segments may comprise relatively wide, substantially incompressible cushion segments, and the second segments may comprise relatively thin, elastic tension segments. During constriction of the band, adjacent incompressible cushion segments form a progressively narrowing angle, for example, a substantially V-shaped surface. A tension segment is located between the adjacent cushion segments and forms the vertex of the angle or V.

In some embodiments, the cushion segments and tension segments form an inner circumference of the loop configuration having a generally star-shape, defined by the contact region. Deformation of the star-shape during adjustment substantially or entirely prevents pinching of tissues, as the cushion segments roll forward one another without gaps therebetween thus pushing the tissue inwardly.

More specifically, in some embodiments, the contact region defines alternating convex stomach-facing surfaces and concave stomach-facing surfaces. The convex organ facing surfaces may be defined by the cushion segments and the convex organ facing surfaces are defined by the tension segments located between adjacent cushion segments. During constriction of the band, the convex organ-facing surfaces may maintain their shape while folding at the tension segments inwardly toward one another. This mechanism and structure causes the tissues of the stomach to be pushed outwardly from the band constriction without the tissues becoming entrapped and/or pinched by the contact region.

In addition, the structure of the contact region, including cushion segments and tension segments, may be advantageously structured to maintain mechanical stability of the band. For example, the tension segments provide a means for maintaining positioning of the cushion segments and by substantially preventing the contact region of the band from creasing, folding or rolling out of position while the band is implanted in the body around the duct or organ, for example, the stomach.

In some embodiments, the contact region comprises a membrane, for example, a somewhat tubular-shaped elastic membrane encompassing, secured to or defining the cushion segments. In one embodiment, portions of the membrane may form the tension segments between adjacent cushion segments.

In one embodiment, the cushion segments are formed of individual incompressible molded elements in contact with or spaced apart from one another, and affixed to the membrane. The cushion segments may be spaced apart by portions of the elastic membrane which are stretched under tension.

The cushion segments may be located on an internal surface of the membrane or alternatively may be located on an external surface of the membrane. In one embodiment, the cushion segments are located on an external surface of the membrane and are overmolded to the membrane.

In another feature of the invention, membrane may include structure, for example, corrugations or indentations, for facilitating expansion of the membrane during adjustment of the loop. For example, such corrugations can be located and structured to minimize the force required to elongate or stretch the membrane in the radial direction during tightening of the band. The corrugated surfaces of the membrane reduce membrane deformation energy by allowing the membrane to unfold rather than stretch during adjustment.

The mechanism for enabling adjustment may comprise an electronic interface, for example, an implantable electronic interface, connected to the band, and a control, for example an external control unit, capable of communicating with the interface to regulate the constriction of the band about said organ or duct.

These and other features of the present invention may be more clearly understood and appreciated upon consideration of the following Detailed Description and the accompanying Drawings.

BRIEF DESCRIPTION OF THE DRAWINGS

FIG. 3 shows a perspective view of the contact region shown in FIG. 1.

FIG. 3A shows a cross-sectional view of the contact region taken along lines 3A-3A of FIG. 3.

FIG. 4A shows an elevation view of the contact region shown in FIG. 1.

FIG. 4B shows an elevation view of an alternative contact region in accordance with another embodiment of the invention.

FIG. 4C shows a perspective view of the alternative contact region shown in FIG. 4B.

FIG. 5A shows a cross-sectional view of the band shown in FIG. 1.

FIG. 5B shows a cross-sectional view of the band taken along lines 5B-5B of FIG. 5A.

FIG. 5C shows a perspective, cutaway view of the band in a fully open position.

FIG. 5D shows a perspective, cutaway view of the band in a constricted position.

Each of FIGS. 22A-22H is a view illustrating steps in a method of laparoscopically implanting the system of the present invention.

Figure 23:
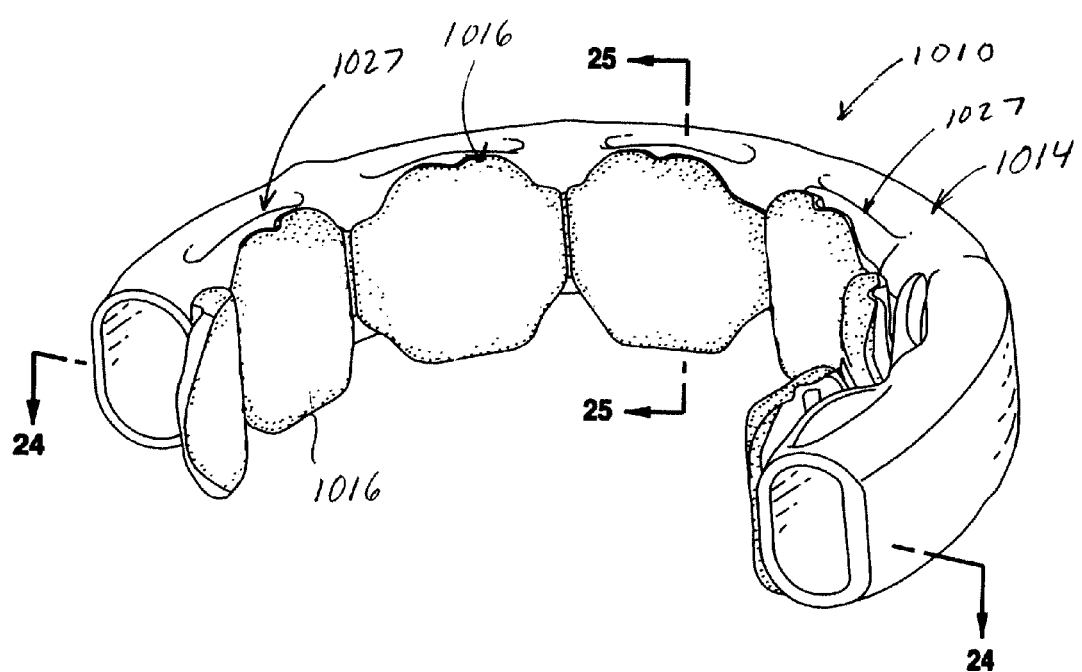

FIG. 23 is a perspective view of a contact region including a membrane and overmolded incompressible cushions of a gastric band of the present invention.

Figure 24:
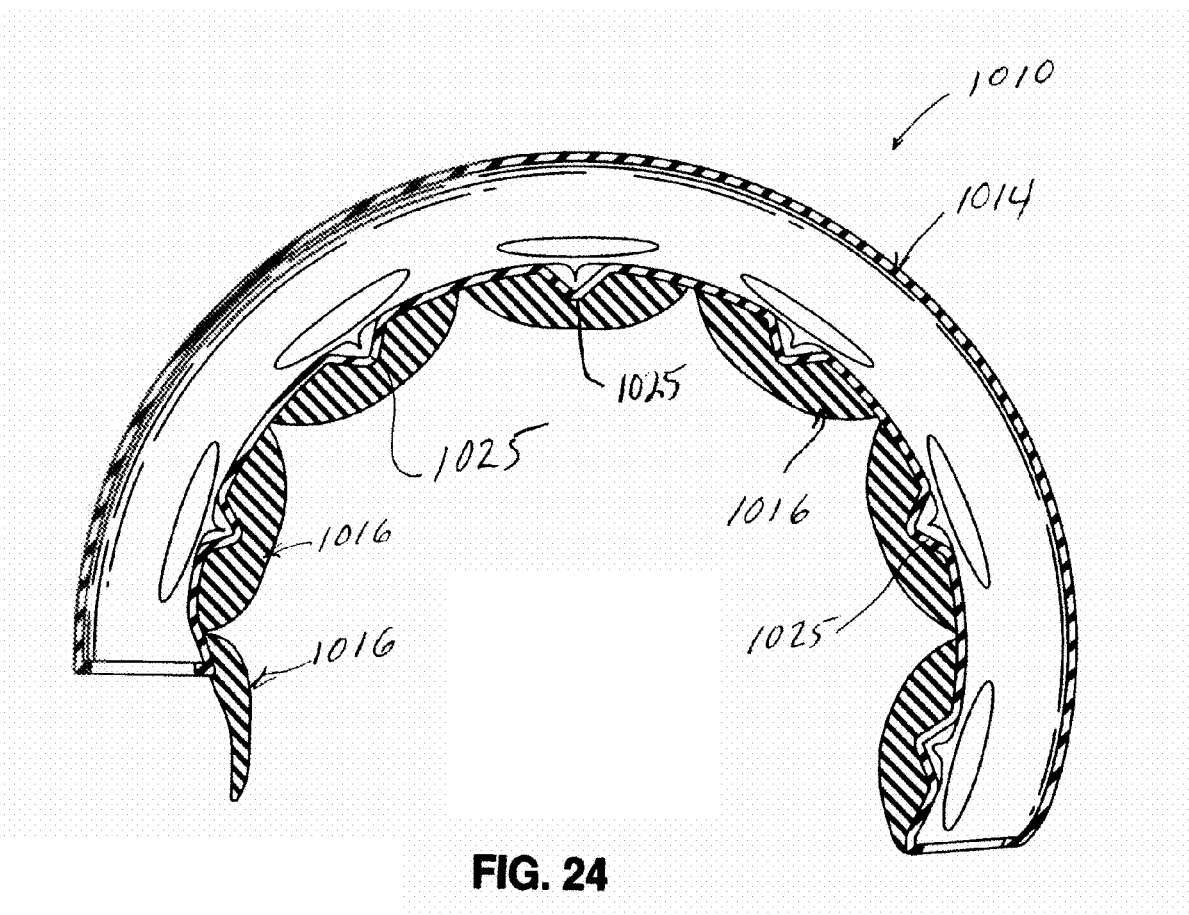
Figure 25:
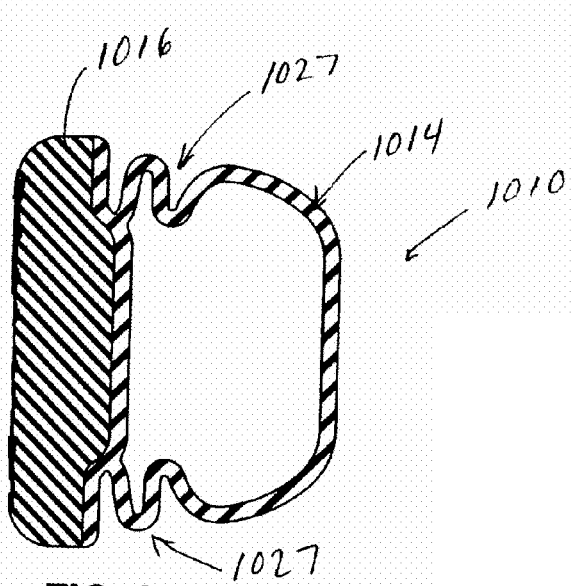

FIGS. 24 and 25 are cross sectional views of the contact region shown in FIG. 23 taken along line 24-24 and line 25-25, respectively.

FIGS. 25-27A show another advantageous feature of the embodiment of the invention shown in FIG. 24.

DETAILED DESCRIPTION

Figure 1:
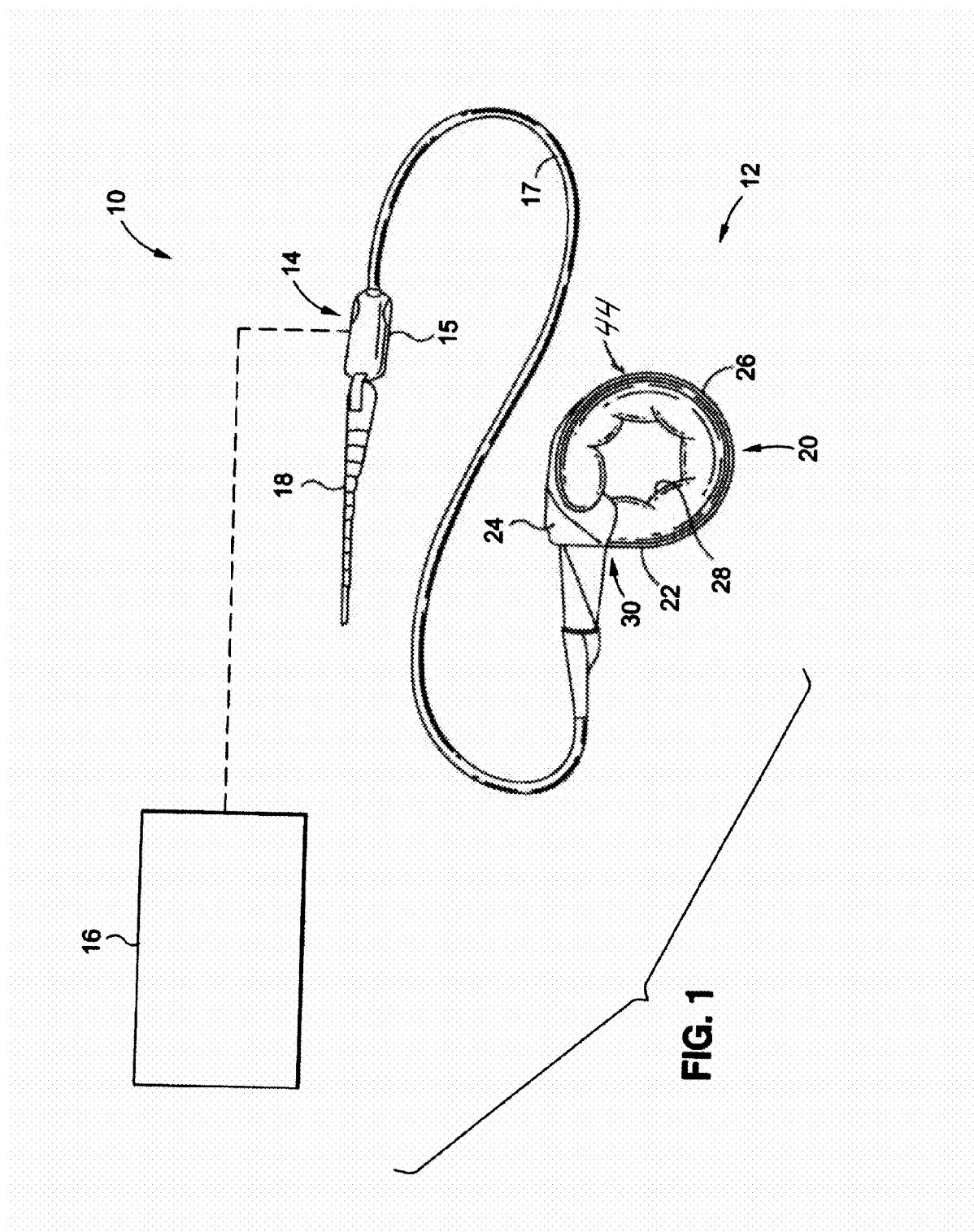
FIG. 1 shows a schematic representation of one embodiment of the present invention, the system including a band including a contact region, an interface including an antenna/controller pod, and an external control.

Turning now to FIG. 1, an embodiment of a system of the present invention is generally shown at 10. In one aspect of the invention, the system 10 is useful for regulating the functioning of an organ or duct (not shown) for example, a stomach. In one embodiment, the system 10 is a gastric banding system useful in the treatment of obesity and/or obesity related diseases.

It is to be understood that although much of the following description is generally directed to gastric banding systems of the invention, the present invention is in no way limited thereto. Other embodiments of the invention may be applied to regulate the functioning of other body organs or ducts, such as in the treatment of gastro-esophageal reflux disease, urinary or fecal incontinence, colostomy, or to regulate blood flow.

In this exemplary embodiment, the system 10 generally comprises an implantable portion 12 including an adjustable band 20, an interface 14 including an antenna/controller pod 15, and a control 16 in communication, for example, telemetric communication, with the pod 15. Pod 15 may be connected to the band 20 by means of antenna cable 17 and may include removable tag 18 for facilitating laparoscopic positioning thereof.

Laparoscopically implanted gastric bands and their use in the treatment of obesity are now well known. Generally, in accordance with the present invention, the band 20 is structured to be implantable in a patient, for example, laparoscopically implantable, around an upper region of the patient's stomach, thereby forming a stoma that restricts food intake and provides feelings of satiety. The inner diameter of the band 20 is adjustable in vivo in order to enable a physician or patient to achieve most desirable stoma size, and the best clinical results.

The band 20 includes a first end 22 and a second end 24, a distal region 26 and a proximal region 28, and a connector 30 configured to couple the first end 22 with the second end 24 of the band 20 such that the band 20 is formable into a loop configuration, as shown.

When the band 20 is formed into said loop configuration, the proximal region 28 forms an inner circumferential surface which at least partially circumscribes and contacts the organ or duct, for example, the stomach, to be regulated or controlled.

Generally, by loosening or tightening the band 20 about the stomach, regulation and/or functioning of the stomach can be controlled or adjusted. When not connected at first and second ends 22, 24, the band 20 can be temporarily straightened in order to facilitate surgical implantation, for example, via laparoscopic techniques.

Figure 2:
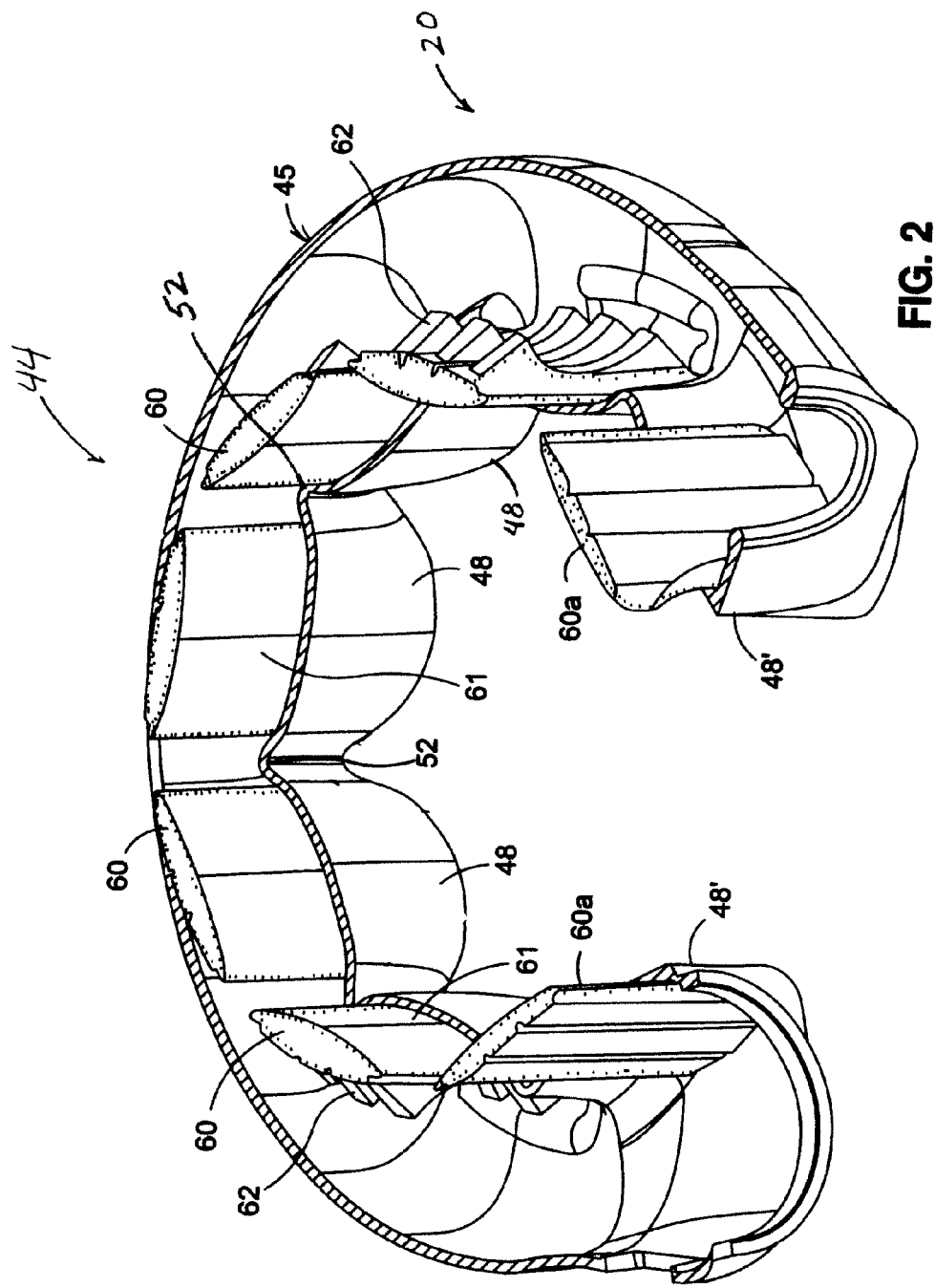
FIG. 2 shows a perspective, cutaway view of the contact region shown in FIG. 1.

The system 10 further comprises a contact region 44 disposed between the first and the second ends 22, 24 of the band 20. Turning now to FIGS. 2 and 3, the contact region 44 may comprise, at least in part, an elastic component made of, for example, a molded silicone elastomer. The elastic component comprises a membrane 45 having a generally tubular form which covers or encases the internal mechanisms of the band 20, for example, gastric band tightening mechanisms such as those to be described hereinafter. The membrane 45, when at rest, may have an arcuate or C-shaped form.

As shown in FIG. 2, contact region 44 comprises first segments 48 and second segments 52 arranged in a generally alternating manner. The first segments 48 may be defined by generally planar and/or convex stomach-facing surfaces, i.e. proximal surfaces, of the contact region 44. The second segments 52 may be defined by generally concave exterior surfaces generally forming indentations between the first segments 48.

In some embodiments, the first segments 48 comprise cushion segments 60. The cushion segments 60 are spaced apart from one another by the second segments 52. The cushion segments 60 may be made of non-compressible material, for example, a silicone elastomer.

In one aspect of the present invention, a suitable incompressible material making up the cushions is a moldable material that has substantially constant density throughout and maintains its volume when deformed. The volume of incompressible materials cannot be reduced more than a nominal amount (e.g., about 5%) when subjected to static compression, or external pressure. The cushions may be a soft silicone material that is a deformable, resilient solid or a gel.

The cushion segments 60 may be made of a material that has a different durometer, for example, is softer, than the material forming the membrane 45. In a specific embodiment, the cushions comprise a soft, molded silicone elastomer material having hardness of 5 Shore A. The membrane comprises a soft molded silicone elastomer material having a hardness of 30 Shore A.

In one embodiment, cushions 60 may be structured to provide form, definition, support and/or structural integrity to the first segments 48. The second segments 52 may be portions of the membrane 45 which are stretched under tension. The second segments may be structured to provide stability to the contact region 44 and to maintain positioning, for example, circumferential positioning, of the cushions 60 during use of the system 10.

Turning now specifically to FIG. 3, the first segments 48 may have a first axial width W1, and the second segments have a second axial width W2 which is less than the first axial width W1.

In the shown embodiment of the invention, the contact region 44 includes seven first segments 48 (including 48'), each first segment being generally equally spaced apart by intermediate second segments 52. In other embodiments of the invention, contact region 44 includes at least three first segments, at least four first segments, at least five first segments, or at least six first segments. In other embodiments of the invention, the contact region 44 includes more than seven first segments, for example, up to ten first segments or more.

In another aspect of the invention, membrane 45 may be structured to facilitate expansion in a radial direction during adjustment of the inner circumference of the band 20. For example, turning now to FIG. 3, membrane 45 may include radially expandable surfaces 56. For example, membrane 45 includes one or more corrugations 58.

In the shown embodiment, the corrugations 58 are generally aligned with the cushion segments 60. As shown in FIG. 3A, the corrugations 58 may be defined by convolutions 58a defined in an upper surface and lower surface of the membrane 45. The corrugations 58 may be placed to minimize the force required by the actuating mechanism to elongate the membrane 45 in the radial direction. Rather than requiring excessive stretching of the membrane, the membrane unfolds during adjustment.

In the shown embodiment, certain first segments 48 include corrugations 58 and other first segments (e.g. first segments 48') do not include corrugations. For example, intermediate first segments 48 include corrugations 58 and terminal first segments 48' do not include corrugations.

The presently described and shown corrugated structure of the contact region 44 may function to facilitate controlled expansion and/or contraction of the first segments 48, for example, during adjustment of the inner circumference of the band. In some embodiments of the invention, the corrugated surfaces 56 function, at least in part, to decrease the level of force required to adjust the inner circumference of the loop.

In some embodiments, the contact region 44 includes first cushions 60 and second cushions 60a which are configured somewhat differently than first cushions 60. In the shown embodiment, first cushions 60 are located on intermediate first segments 48 and second cushions 60a are located on terminal first segments 48' (i.e. those first segments located at the extremities of the contact region 44).

More specifically, in the embodiment shown in FIG. 2, each first cushion 60 includes a substantially planar or convex face 61 and at least one or more distal projections 62. For example, each cushion 60 includes three longitudinal, arcuate projections 62 as shown. A cross-sectional view of first cushion 60 having these features is also shown in FIG. 3A.

FIG. 4A shows an elevation view of the contact region 44 (cushions not shown) in order to illustrate width W1 of first segment 48 relative to width W2 of second segment 52 of contact region 44. In an exemplary embodiment of the invention, W1 is about 17 mm and W2 is about 13 mm.

FIG. 4B shows an elevation view of an alternative contact region 44' in accordance with the invention. Contact region 44' is identical to contact region 44 shown in FIG. 4A, with a primary difference being that first segment width W1' of contact region 44' is greater than first segment width W1 of contact region 44. That is, W1'>W1. The additional width of first segment width W1' is provided by upper and lower protuberances 66 on first segments 48'. In an exemplary embodiment, W1' is about 19 mm and W2 is about 13 mm. FIG. 4C shows a perspective view of contact region 44' having first segments 48' with protuberances 66.

Turning now to FIGS. 5A-5D, an exemplary inner mechanism of the band 20 which enables adjustment of the inner circumference of the loop configuration will now be described. Band 20 may comprise a flexible tension element 132 having fixed end 133 mounted to first end 22 of band 20 and another end 134 that is coupled to an actuator 135 at second end 24 of adjustable element 20. Tension element 132 is slidingly disposed within a substantially cylindrical tube of axially compressible material 136. When tension element 132 is pulled through actuator 135, compressible material 136 is compressed and the diameter of loop opening 137 is reduced.

Turning now specifically to FIGS. 5B through 5D, compressible material 136 may be surrounded on a distal face 137 thereof with a flexible, relatively sturdy elastomeric material, such as silicone element 138. Both compressible material 136 and silicone element 138 are enclosed within the membrane 45 of contact region 44.

Figure 5F:
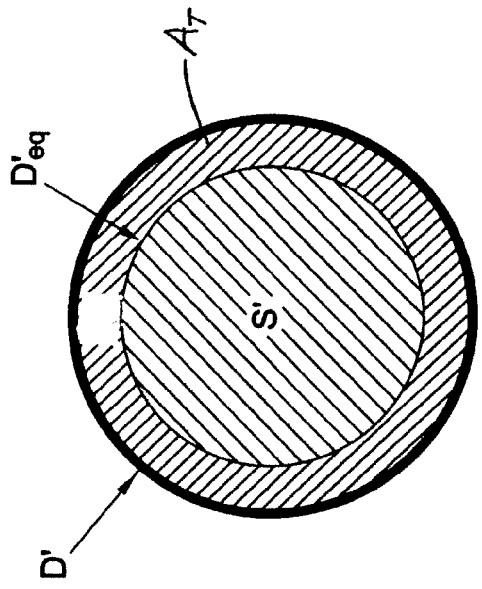
FIGS. 5E and 5F are schematic representations of an amplified adjustment feature of an embodiment of the present invention.
Figure 5E:
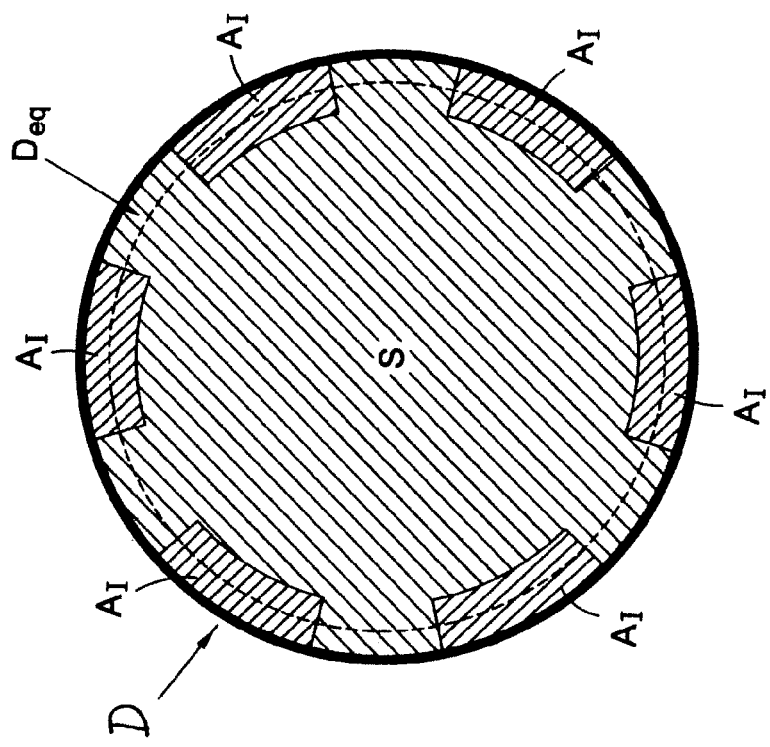

In one aspect of the invention, the band 12 may be structured to provide an amplified adjustment feature. This concept is illustrated in FIGS. 5E and 5F, and in FIGS. 26 through 27A.

The incompressible cushion segments 60 provide enhanced and more efficient control of adjustment of the inner diameter of the band 20. FIGS. 5E and 5F are schematic representations of the cross-section of the band in the open configuration and constricted configuration, respectively. Outer diameter D represents the outer diameter of axially adjustable portion of the band 20. Areas of individual cushion regions 60 are represented by areas $A_I$ in FIG. 5E (open configuration). The total area occupied by the individual cushion regions is represented as annular area $A_T$ in FIG. 5F (constricted configuration). Surface S represents the available lumen around the stomach (or other organ or duct being controlled or regulated) and diameter Deq represents an equivalent diameter, that is, the diameter of a circle having the same surface area as S.

When the loop is constricted from the fully open state, diameter D (FIG. 5E) becomes D' (FIG. 5F), the surface S becomes S' and the equivalent diameter Deq becomes D'eq. Because the cushions occupying $A_I$ are incompressible, the total surface area $A_T$ occupied by the cushions does not change. The equivalent diameter Deq decreases more rapidly than the diameter D.

For example, D=29 mm in a fully open position and a total surface of the incompressible cushions $A_T$ equal to about 120 square mm: S=540.52 sq mm and Deq=26.2 mm. When in fully closed position, D'=19 mm: S'=163.53 sq mm, and D'eq=14.4. Thus D-D'=10 mm, and Deq-D'eq=11.8 mm, which provides an "amplification factor" of about 1.18. Thus, by changing the values of D, D' and $A_T$, the amplification factor can be controlled.

The substantially incompressible cushion segments allow a relative restriction of the lumen during adjustment greater than without substantially incompressible cushion segments. That greater relative restriction arises from the fact that the cross-section of the substantially incompressible cushion segments remains constant during adjustment, whereas the area of the lumen decreases during closure, so that the ratio (cushion cross-section)/(lumen) increases. Accordingly, the substantially incompressible cushion segment effect on lumen restriction increases during closure.

Figure 5H:
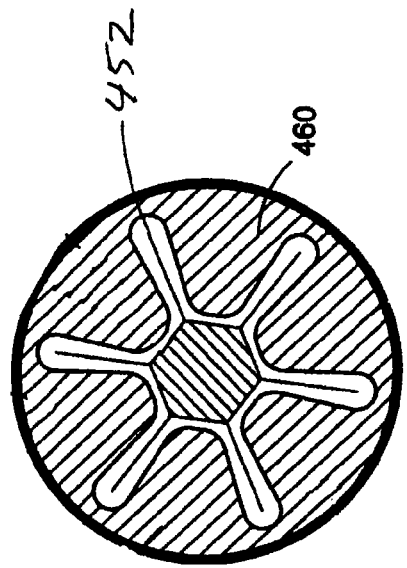
FIGS. 5G and 5H are simplified schematic representations of another embodiment of the invention.
Figure 5G:
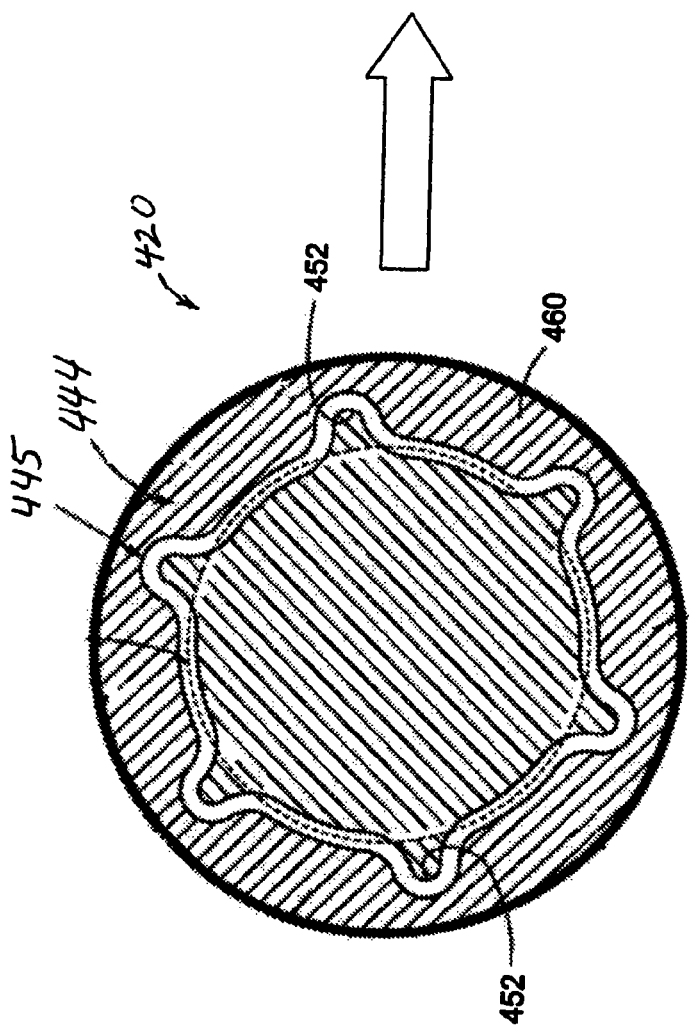

FIGS. 5G and 5H show a simplified schematic representation an embodiment of the invention in which contact region 444 comprises an elastic membrane 445 and a single continuous, incompressible cushion segment 460 instead of the individual, separate cushion segments 60 shown in FIG. 2. Other than cushion segment 460 being a single substantially continuous cushion segment rather than a plurality of individual separate cushion segments 60, the band 420 may be identical to band 20. The continuous cushion segment 460 is configured or shaped to accommodate tension segments 452 of the membrane 445. For example, the continuous cushion segment 460 has a variable thickness, with the thickest regions functioning similarly to incompressible cushion regions 60 described elsewhere herein. FIG. 5H shows bending of tension regions 452 and deformation of incompressible cushions 60 during the constriction of the loop.

Turning back to FIG. 5A, band 20 may further comprise member 140 of a relatively rigid material. By its structural rigidity, member 140 imposes a generally circular arc shape for the entirety of band 20. In some embodiments of the invention, rigidity of band 140 functions to prevent the exterior diameter of band 12 from changing during adjustment of the internal diameter of the loop.

Generally, an increase or reduction of the length of tension element 132 results in reversible radial displacement at the internal periphery of the band 20. This in turn translates into a variation of internal diameter of the loop from a fully open diameter to a fully closed diameter.

In various embodiments of the invention, the diameter of the opening 137 formed by the band 20 may be between about 25 mm or about 35 mm in a fully dilated position (e.g. see FIG. 5C). The diameter of the opening 137 may be between about 15 mm and about 20 mm when the band 20 is in a fully constricted position (e.g. see FIG. 5D).

Figure 6A:
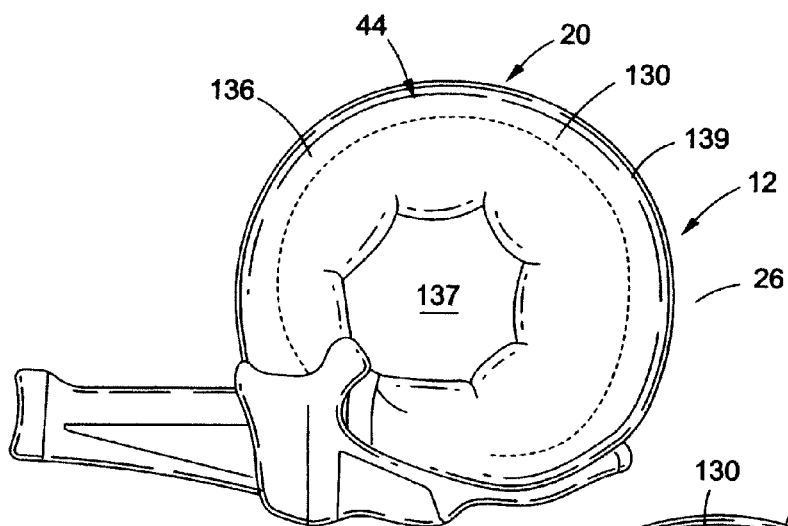
FIGS. 6A through 6C show plan views of the band at different levels of constriction.
Figure 6B:
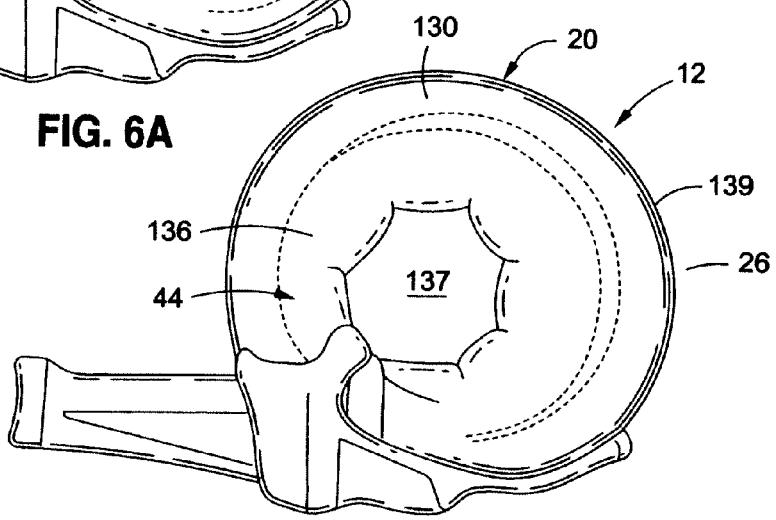
Figure 6C:
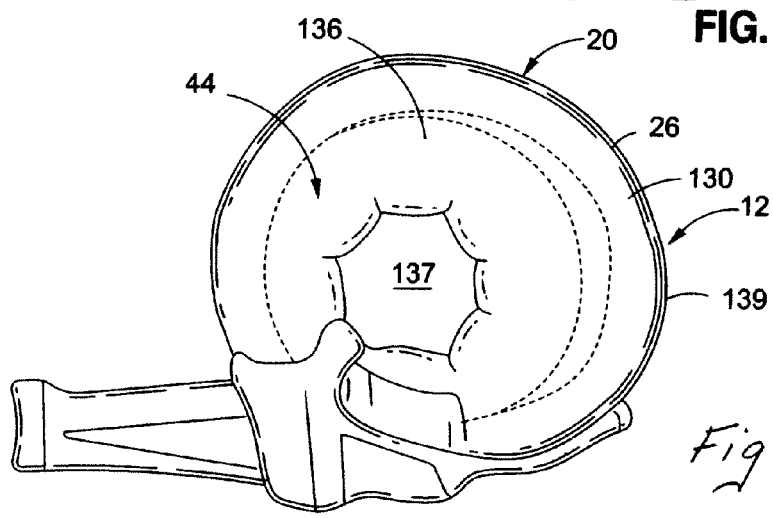

FIGS. 6A, 6B and 6C show the band 12 at progressively increased levels of constriction, with FIG. 6A showing the opening 137 being larger than in FIG. 6B, which shows the opening 137 larger than in FIG. 6C. In the shown embodiment of the invention, while diameter of opening 137 is adjustable, the diameter an outer circumferential surface 139 of the band 12 remains relatively fixed during adjustments of the opening 137. Membrane 45 of contact region 44 stretches or unfolds as described elsewhere herein, as axially compressible material 136 moves apart from distal element 130 and band (not visible in FIGS. 6A-6C) and opening 137 constricts. (See also FIG. 5D).

Figure 7:
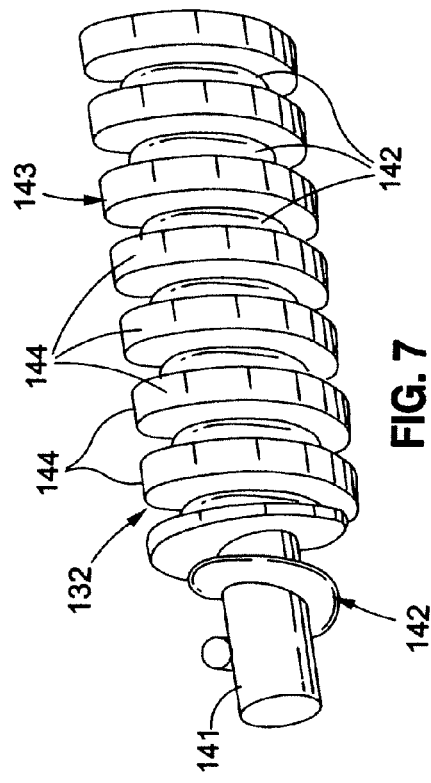
FIG. 7 is a partial perspective view of a screw thread portion of a tension element useful in the band of the system of the invention.

Referring now to FIG. 7, tension element 132 is described. In some embodiments, tension element 132 has sufficient flexibility to permit it to be formed into a substantially circular shape, while also being able to transmit the force necessary to adjust the inner diameter of the loop. Tension element 132 may comprise flexible core 141, for example, comprising a metal alloy wire of circular cross section, on which is fixed, and wound coaxially, at least one un-joined coil spring which defines a screw thread pitch.

Tension element 32 may comprise two un-joined coil springs that form a screw thread: first spring 142, wound helicoidally along the flexible core 141, and second spring 143 of greater exterior diameter. Second spring 143 preferably comprises coils 144 of rectangular transverse section, so as to delineate a flat external generatrix. First spring 142 is interposed between coils 144 of the second spring 143 to define and maintain a substantially constant square screw thread pitch, even when the tension element is subjected to bending.

Second spring 143 may be made by laser cutting a cylindrical hollow tube, e.g., made from stainless steel, or alternatively, by winding a wire with a rectangular, trapezoidal or other cross-section. When helically intertwined with first spring 142, coils 144 of second spring 143 are activated with an intrinsic elastic compression force from the adjacent coils of first spring 142. First spring 142 is intertwined between the coils of second spring 143. First spring 142 is fixedly joined to flexible core 141 at one end. At the second end, a crimped cap 145 (see FIG. 8) is located a short distance from the ends of springs 142 and 143 to allow for small extensions, for example, to accommodate flexion of tension element 132 and/or to limit this extension to keep the thread pitch substantially constant.

Figure 8:
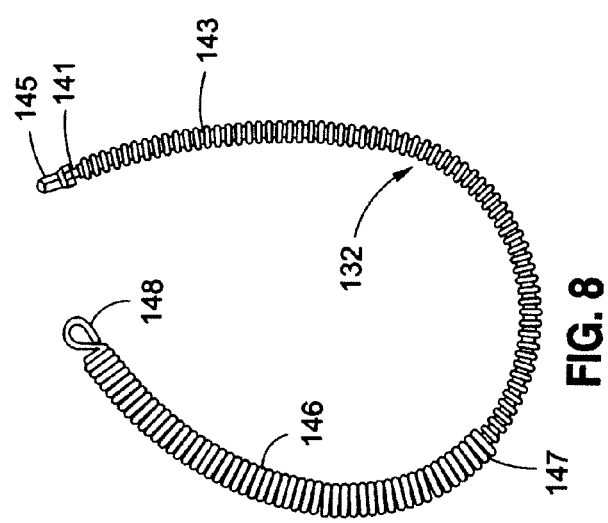
FIG. 8 is a perspective view of an entire tension element shown in FIG. 7.

Referring now to FIG. 8, free end 134 of tension element 132 includes crimped cap 145. Second spring 143 includes coils having a square transverse section. Flexible core 141 extends through first and second springs 142 and 143, and terminates close to cap 145. In one embodiment of the invention, tension element 132 further comprises third spring 146 that is coupled to flexible core 141, and first and second springs 142 and 143 at junction 147. Third spring 146 includes loop 148 at the end opposite to junction 147, which permits the tension element 132 to be fixed at first end 22 of band 20.

Figure 9:
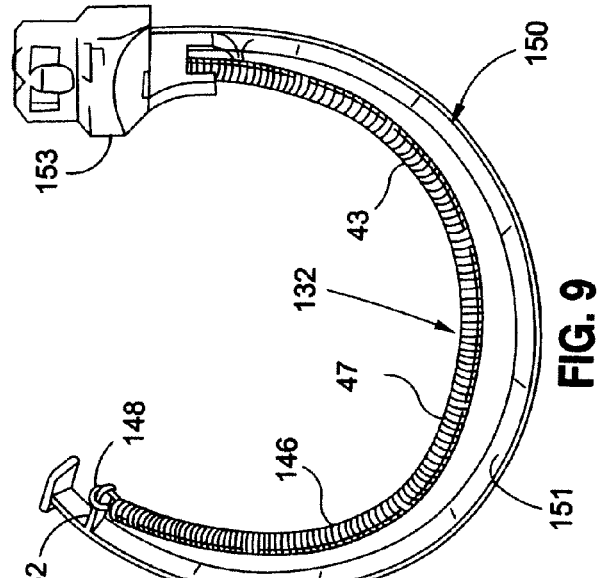
FIG. 9 is a perspective view of the tension element of FIG. 8 coupled to a rigid distal peripheral portion in the band of the system of the invention.

With respect to FIG. 9, tension element 132 is shown disposed within a skeleton 150 of the band 20. Skeleton 150 includes layer 151 that forms a distal periphery, anchor 152 that accepts loop 148 of tension element 132, and actuator housing 153. Skeleton 150 may be made of a high strength moldable plastic.

Figure 10:
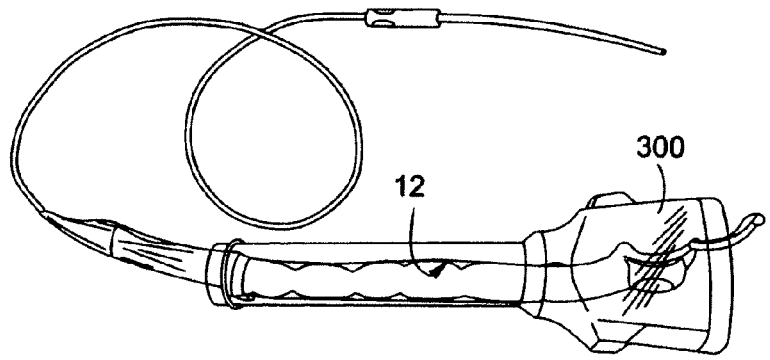
FIG. 10 is a perspective view of the band of the system in a straightened configuration and located within a trocar to facilitate implantation.

In accordance with another aspect of the invention, third spring 146 permits band 12 to be straightened for insertion through a trocar, for example a 18 mm trocar, despite a differential elongation of the skeleton 150 and tension element 132. This feature is illustrated in FIG. 10 which shows band 12 disposed in a trocar 300 in order to facilitate laparoscopic implantation of the band 12.

Figure 11:
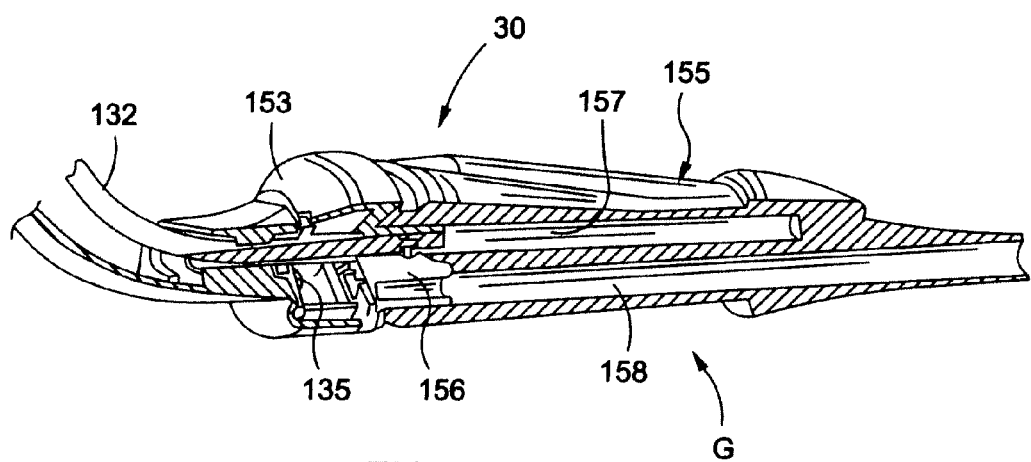
FIG. 11 is a cross-sectional view of an actuator housing on an end of the band.

Referring now to FIG. 11, in the shown embodiment, connector 30 includes housing 155 having recessed portion 156, tension element cavity 157 and cable lumen 158. Recess 156 is configured to accept actuator housing 153 of skeleton 150, so that as tension element 132 is drawn through actuator 135 it extends into tension element cavity 157. Cable lumen 158 extends through housing 155 so that cable 124 may be coupled to actuator 135. Housing 155 may be grasped in area G using atraumatic laparoscopic graspers during implantation.

Figure 12:
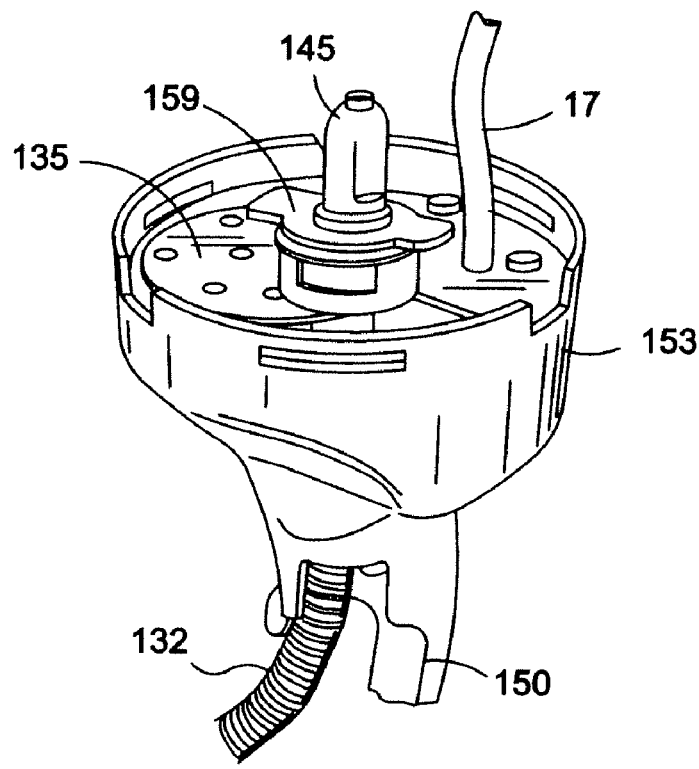
FIG. 12 is a perspective view of an actuator in the housing shown in FIG. 11.

In FIG. 12, actuator housing 153 of skeleton 150 is shown with actuator 135 and tension element 132 disposed therethrough. Antenna cable 17 is coupled to motor (not shown) disposed within actuator housing 153. Tension element 132 is in the fully opened (largest diameter) position, so that crimped cap 145 contacts printed circuit board 159 of the reference position switch described below with respect to FIG. 15.

Figure 13:
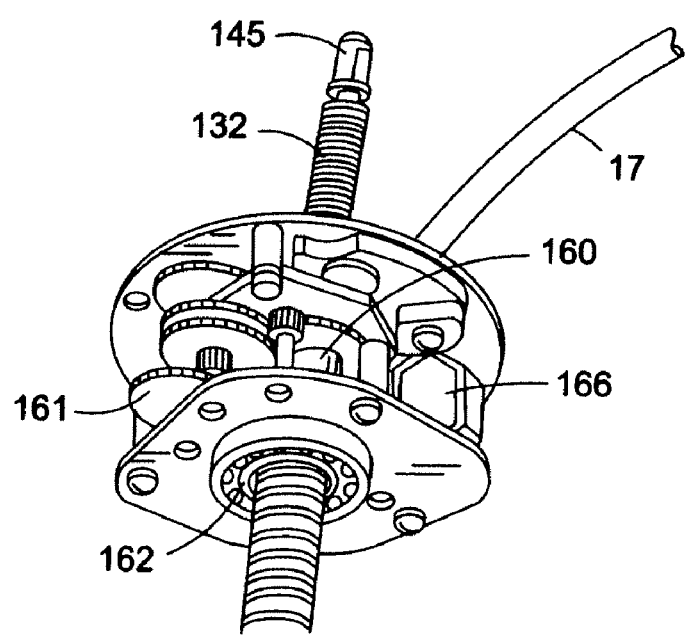
FIG. 13 is a perspective of the tension element engaged with the actuator shown in FIG. 12.
Figure 14:
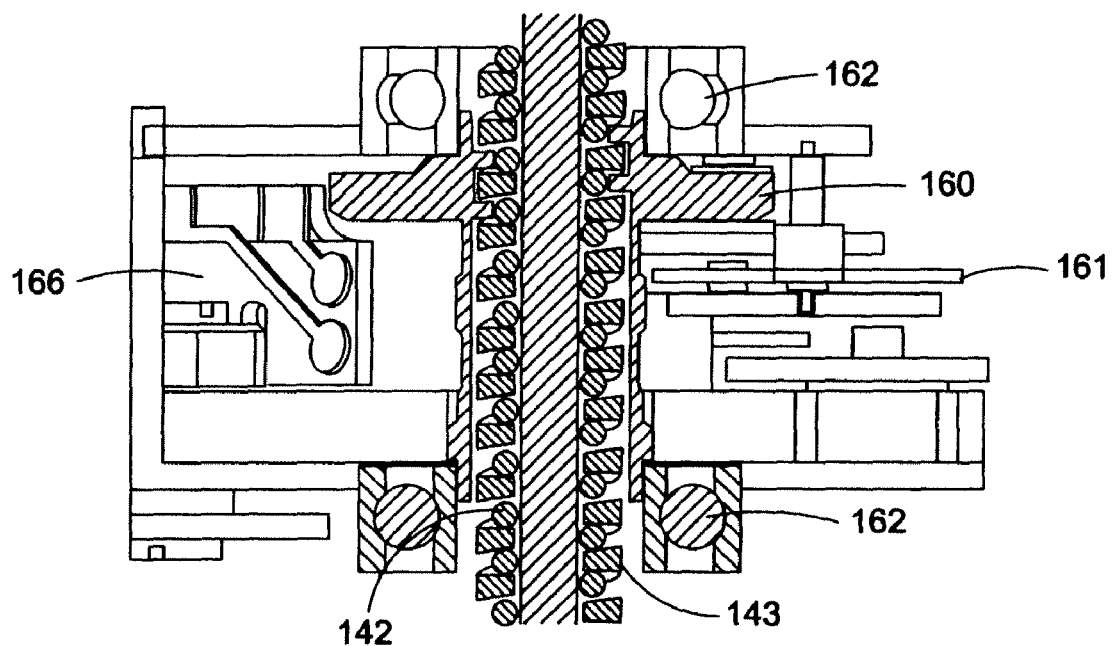
FIG. 14 is a cross-sectional view depicting the construction of the actuator shown in FIG. 12.

With respect to FIGS. 13 and 14, actuator 135 includes motor 166 coupled to antenna cable 17 that drives nut 160 through gears 161. Nut 160 is supported by upper and lower bearings 162 to minimize energy losses due to friction. Nut 160 is self-centering, self-guiding and provides high torque-to-axial force transfer. In addition, nut 160 is self-blocking, meaning that nut 160 will not rotate due to the application of pushing or pulling forces on tension element 132. This condition may be achieved by ensuring that the height (h) of the thread divided by the circumference of the screw ($2\pi R$) is less than the arctangent of the friction coefficient (p):

$$h/(2\pi R) < \arctan(\mu)$$

Gears 161 preferably are selected to provide good mechanical efficiency, for example, with a reduction factor greater than 1000. In addition, the volume of the actuator depicted in FIGS. 13 and 14 may be quite small, with a total volume less than 1 cm$^3$ and a diameter less than 12.5 mm, so that the device may easily pass through a standard trocar. In a preferred embodiment, gears 161 are selected to provide a force of more than 2 kg on the screw thread of the tension element at an electrical consumption of only 50 mW. The gears and other components of actuator 135 may be made of stainless steel or other alloys like Arcap (CuNiZn), or can be gold plated to permit operation in the high humidity likely to be encountered in a human body.

Motor 166 employed in actuator 135 may comprise a Lavet-type high precision stepper motor with a flat magnetic circuit, such as are used in watches. The motor 166 may be a two phase (two coil) motor that permits bi-directional rotation, has good efficiency, and may be supplied with a square wave signal directly by the microcontroller circuitry within antenna/controller pod 15, thus eliminating the need for an interface circuit. Alternatively, the motor employed in actuator 135 may be of a brushless DC type motor. In addition, the motor preferably is compatible with magnetic resonance imaging, i.e., remains functional when exposed to strong magnetic fields used in medical imaging equipment.

Figure 15:
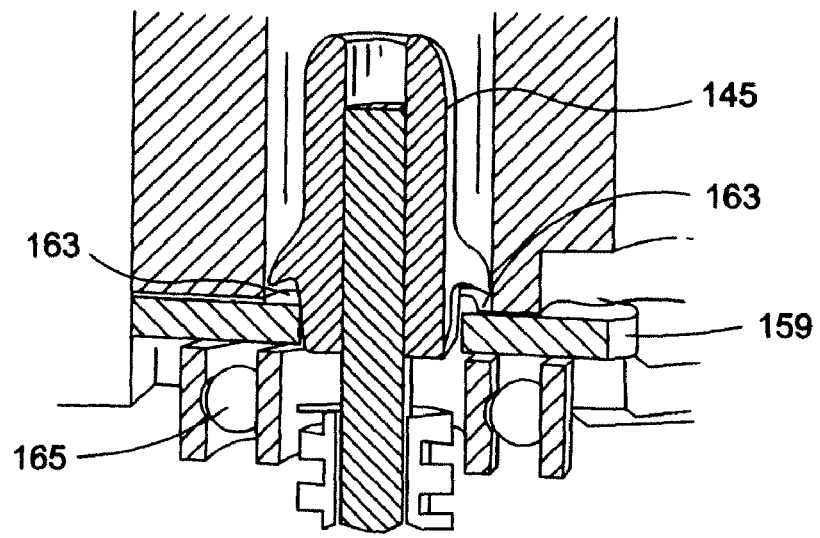
FIG. 15 is a cross-sectional view depicting the construction of a reference position switch useful in the system of the invention.

Referring now to FIG. 15, a reference position switch of an embodiment of the present invention is described. In one embodiment the actuator of the present invention employs nut 160 driven by a stepper motor. Thus, there is no need for the system to include a position sensor or encoder to determine the length of tension element 132 drawn through the actuator. Instead, the diameter of opening 137 may be computed as a function of the screw thread pitch and the number of rotations of nut 160. At least one reference datum point may be provided which may be calculated by using a reference position switch that is activated when band 12 is moved to its fully open position. Crimped cap 145 on the free end of tension element 132 may be used to serve this function by contacting electrical traces 163 on printed circuit board 159 (and also limits elongation of the screw thread). Circuit board 159 is disposed just above bearing 165, which forms part of actuator 135. When crimped cap 145 contacts traces 163 it closes a switch that signals the implantable controller that the band 12 is in the fully open position.

Figure 16A:
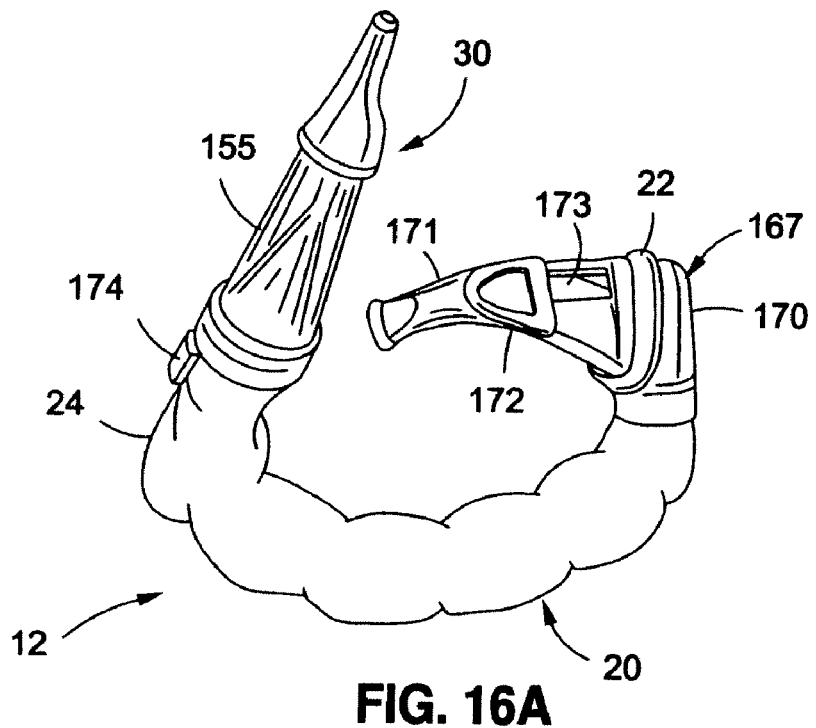
FIGS. 16A and 16B are perspective views illustrating a clip used to close the band of the system of the invention.
Figure 16B:
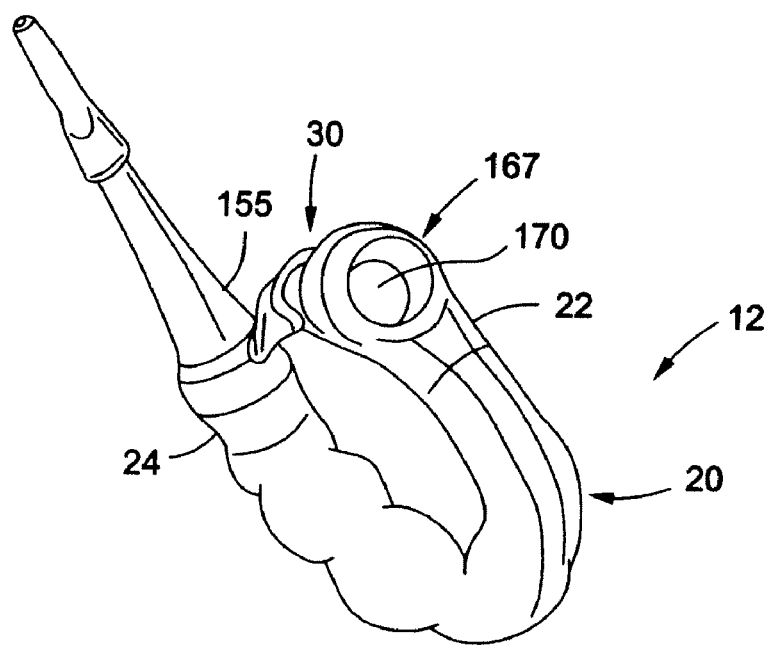

Referring now to FIGS. 16A and 16B, clip 30 may include a clip element 167 on first end 22 of band 20 and the housing 155 on the second end of the band 20. Clip element 167 includes aperture 170, tab 171 having hinge 172 and slot 173. Aperture 170 is dimensioned to accept housing 155 on second end 24 of band 20, while slot 173 is dimensioned to accept flange 174 disposed on second end 24.

An example of a method of coupling the first end 22 with second end 24 during implantation of the band 20 is now described. To couple first end 22 and second end 24, clip element 167 is grasped by the tab 171, and tag 18 of pod 15 (see FIG. 1) is inserted through aperture 170. Clip element 167 is then pulled towards second end 24 so that housing 155 passes through aperture 170 while housing 155 is grasped with atraumatic forceps; the conical shape of housing 155 facilitates this action. Force is applied to tab 171 until slot 173 captures flange 174, thereby securing the first and second ends 22, 24 in the closed position. The physician may subsequently choose to disengage slot 173 from flange 174 by manipulating tab 171 using laparoscopic forceps, for example, to reposition the band 12. In some embodiments, forces inadvertently applied to tab 171 in an opposite direction will cause tab 171 to buckle at hinge 172, but will not cause flange 174 to exit slot 173. Accordingly, hinge 172 of tab 171 prevents accidental opening of clip 30 when the tab 171 is subjected to forces that cause the tab 171 to fold backwards away from housing 155 such as may arise due to movement of the patient, the organ, or bolus of fluid passing through the organ.

Figure 17:
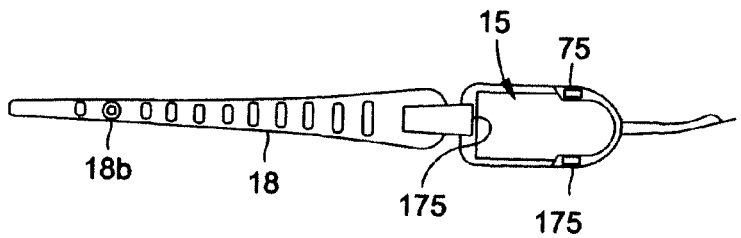
FIG. 17 is a perspective view of the antennae/controller pod of the system shown in FIG. 1.
Figure 18:
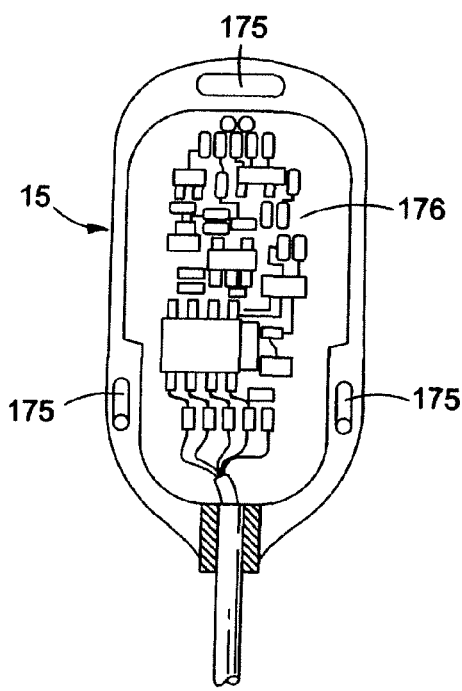
FIG. 18 is a cut-away view of the interior of the implantable antenna/controller pod.
Figure 20:
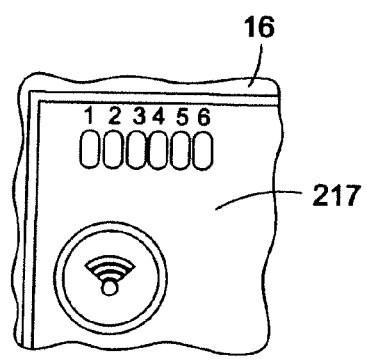
FIG. 20 is a view of a signal strength indicator portion of the control shown in FIG. 1.

With respect to FIGS. 17 and 18, removable tag 18 of antenna/controller pod 15 may include apertures 175. Tag 18 comprises a grip structure that facilitates manipulation and placement of the pod during implantation; after which the tag is removed, for example, using a scissors cut. Tag 18 also includes aperture 18b that allows the use of a suture thread to assist in passing the antenna/controller pod 15 behind the stomach. Holes 175 also are dimensioned to be compatible with standard suture needles from size 1-0 to 7-0 to permit pod 15 to be sutured to the patient's sternum, thereby ensuring that pod 15 remains accessible to the external antenna and cannot migrate from a desired implantation site.

As shown in FIG. 18, antenna/controller pod 15 encloses printed circuit board 176 that carries the antenna and microcontroller circuitry of band (not shown). The antenna receives energy and commands from external control 16 (see FIG. 1), and supplies those signals to the microcontroller, which in turn powers motor 166 of actuator 135 (FIGS. 12 and 13). The circuitry of antenna/controller pod 15 uses the energy received from the incoming signal to power the circuit, interprets the commands received from external control 16, and supplies appropriate signals to the motor of actuator 135. The circuit also retrieves information regarding operation of the motor 166 of actuator 135 and relays that information to external control 16 via the antenna. The circuit board 176 may be covered with a water-resistant polymeric covering, e.g., Parylene, to permit use in the high (up to 100%) humidity environment encountered in the body.

Antenna/controller pod 15 may include a mechanical closure system that is augmented by silicone glue so that the pod 15 is fluid tight. This silicone glue also is used to protect soldered wires.

Actuator 135 may be linked to subcutaneous antenna/controller pod 15 to receive a radio frequency control and power signal. In one embodiment, the motor 166 of the actuator 135 has no internal energy supply, but rather is powered by the receiving circuit of the antenna through a rechargeable energy storage device, such as a capacitor. For example, the receiving circuit converts radio frequency waves received from external control 16 via the antenna into a motor control and power signal. In another embodiment the actuator 135 may be driven via an implantable rechargeable battery.

Figure 19:
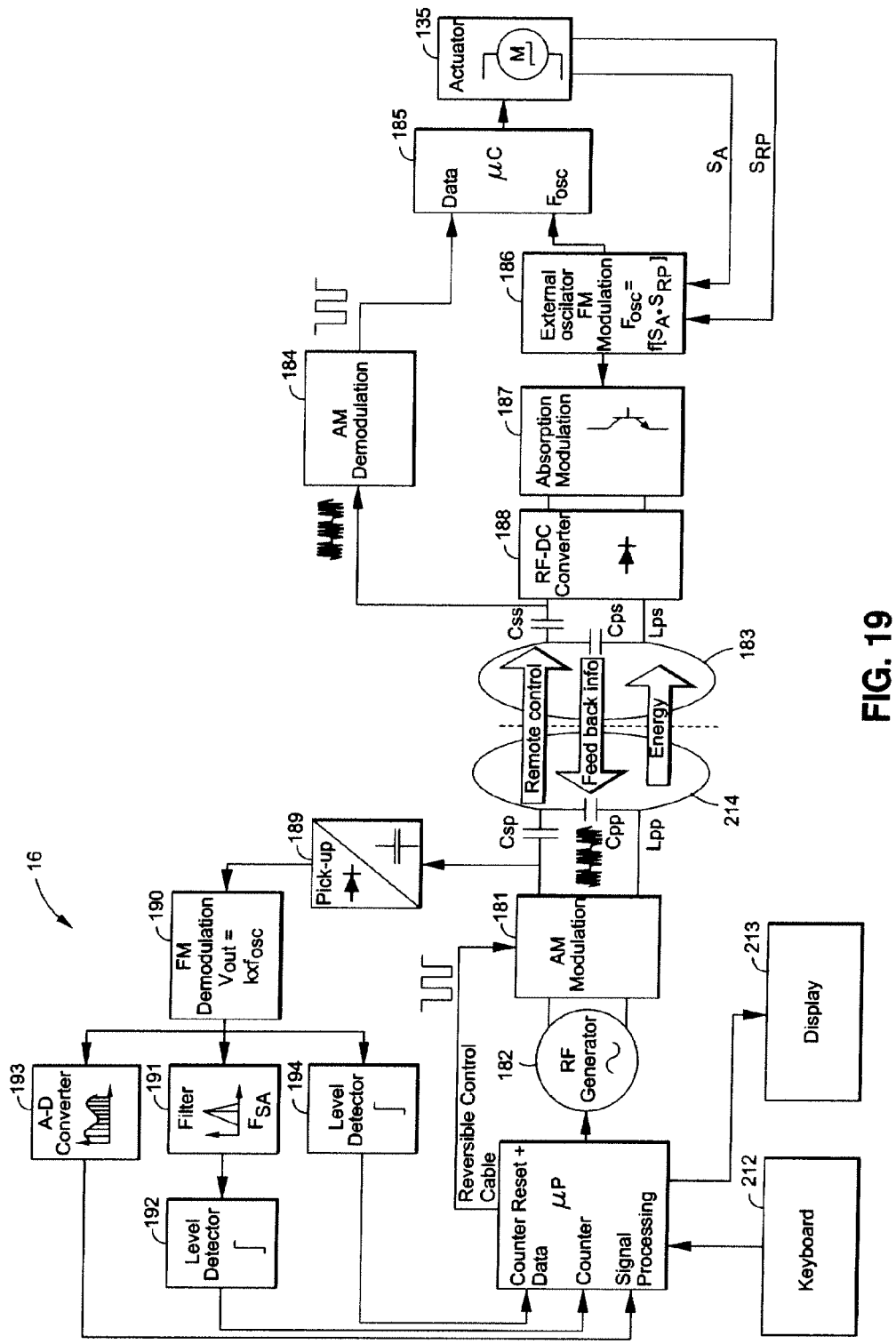
FIG. 19 is a schematic view of telemetric power and control circuitry useful in systems of the invention.

Referring to FIG. 19, one suitable arrangement of circuitry that may be employed in external control 16 of the present invention is described. External control 16 includes microprocessor 180 coupled to a keyboard/control panel 212 and display 213. External control 16 produces a signal comprising one or more data bytes to be transmitted to the implantable antenna/controller pod (not shown) and actuator 135.

External control 16 includes modulator 181 for amplitude modulation of the RF wave from RF generator 182, which signal is emitted by an external antenna 214. The emitted wave is received by antenna 183 in the antenna/controller pod (not shown), where AM demodulator 184 extracts the data bytes from the envelope of received RF signal. The data bytes then are decoded by microcontroller 185. A special code is used that allows easy decoding of the data by microcontroller 185, but also provides maximal security against communication failure.

External oscillator 186, which is a voltage controlled oscillator (VCO), provides a clock signal to microcontroller 185. Oscillator 186 may comprise, for example, a relaxation oscillator comprising an external resistor-capacitor network connected to a discharging logic circuitry already implemented in the microcontroller or a crystal oscillator comprising a resonant circuit with a crystal, capacitors and logic circuits.

Microcontroller 185 interprets the received instructions and produces an output that drives the motor of actuator 135. As discussed above, actuator 135 may comprise a bi-directional stepper motor that drives nut 160 through a series of reducing gears. In one embodiment, the two coils of the stepper motor of actuator 135 are directly connected to microcontroller 185, which receives the working instructions from demodulator 184, interprets them and provides the voltage sequences to the motor coils. When the supply of voltage pulses to the stepper motor stops, the gears are designed to remain stationary, even if a reverse torque or force is applied to nut 160 by tension element 132.

As also described above, use of a stepper motor in actuator 135 makes it is possible to obtain positional information on nut 160 and tension element 132 without the use of sensors or encoders, because the displacement of the tension element is proportional to the number of pulses supplied to the stepper motor coils. Two signals may be employed to ensure precise control, reference position signal $S_{RP}$, generated by the reference position switch of FIG. 15, and the actuator signal $S_A$.

According to one embodiment, signal $S_A$ is the voltage signal taken at one of the outputs of microcontroller 185 that is connected to the motor coils of actuator 135. Alternatively, signal $S_A$ could be derived from the current applied to a motor coil instead of the voltage, or may be an induced voltage on a secondary coil wrapped around one of the motor coils of actuator 135. In either case, signal $S_A$ may be a pulsating signal that contains information on the number of steps turned by the rotor and further indicates whether blockage of the mechanism has occurred. Specifically, if the rotor of the stepper motor fails to turn, the magnetic circuit is disturbed, and by induction, affects signal $S_A$, e.g., by altering the shape of the signal. This disturbance can be detected in the external control, as described below.

Signals $S_A$ and $S_{RP}$ are converted into frequencies using external oscillator 186, so that the voltage level of signal $S_A$ applied to external oscillator 186 causes the oscillator to vary its frequency $F_{OSC}$ proportionally to the signal $S_A$. Thus, $F_{OSC}$ contains all the information of signal $S_A$. When crimped cap 145 and tension element 132 are in the reference position (band 12 is fully open), the reference position switch produces reference position signal $S_{RP}$. Signal $S_{RP}$ is used to induce a constant shift of the frequency $F_{OSC}$, which shift is easily distinguishable from the variations due to signal $S_A$.

If oscillator 186 is a relaxation oscillator, as described above, signals $S_A$ and $S_{RP}$ modify the charging current of the external resistor capacitor network. In this case, the relaxation oscillator may comprise an external resistor-capacitor network connected to a transistor and a logic circuit implemented in microcontroller 185. With $S_A$ and $S_{RP}$, the goal is to modify the charging current of the capacitor of the RC network to change the frequency of the relaxation oscillator. If the charging current is low, the voltage of the capacitor increases slowly and when the threshold of the transistor is reached, the capacitor discharges through the transistor. The frequency of the charging-discharging sequence depends on the charging current.

If oscillator 186 is a crystal oscillator, signals $S_A$ and $S_{RP}$ modify the capacitor of the resonant circuit. In this case, the crystal oscillator circuit preferably comprises a crystal in parallel with capacitors, so that the crystal and capacitors form a resonant circuit which oscillates at a fixed frequency. This frequency can be adjusted by changing the capacitors. If one of these capacitors is a Varicap (a type of diode), it is possible to vary its capacitance value by modifying the reverse voltage applied on it, $S_A$ and $S_{RP}$ can be used to modify this voltage.

In either of the foregoing cases, signals $S_A$ and $S_{RP}$ may be used to modify at least one parameter of a resistor-capacitor (RC) network associated with the oscillator 186 or at least one parameter of a crystal oscillator comprising the oscillator 186.

Referring still to FIG. 19, signals $S_A$ and $S_{RP}$, derived from the stepper motor or from the output of the microcontroller 185, may be used directly for frequency modulation by the oscillator 186 without any encoding or intervention by the microcontroller 185. By using oscillator 186 of microcontroller 185 as part of the VCO for the feedback signal, no additional components are required, and operation of micro controller 185 is not adversely affected by the changes in the oscillator frequency $F_{OSC}$. The oscillating signal $F_{OSC}$ drives voltage driven switch 187 for absorption modulation, such that feedback transmission is performed with passive telemetry by FM-AM absorption modulation.

More specifically, signal $F_{OSC}$ drives switch 187 such that during the ON state of the switch 187 there is an increase in energy absorption by RF-DC converter 188. Accordingly, therefore the absorption rate is modulated at the frequency $F_{OSC}$ and thus the frequency of the amplitude modulation of the reflected wave detected by external control 16 contains the information for signal $S_A$. As discussed below, pickup 189 in external control 16 separates the reflected wave where it can be decoded by FM demodulation in demodulator 190 to obtain signal $S_A$. This method therefore allows the transmission of different signals carried at different frequencies, and has the advantage that the ON state of switch 187 can be very short and the absorption very strong without inducing an increase in average consumption. In this way, feedback transmission is less sensitive to variation in the quality of coupling between the antennas 183 and 214.

In external control 16, the feedback signal $F_{OSC}$ is detected by the pickup 189 and fed to FM demodulator 190, which produces a voltage output $V_{OUT}$ that is proportional to $F_{OSC}$. $V_{OUT}$ is fed to filter 191 and level detector 192 to obtain the information corresponding to the actuator signal $S_A$, which in turn corresponds to the pulses applied to the stepper motor coil. Microprocessor 180 counts these pulses to calculate the corresponding displacement of the tension element 32, which is proportional to the number of pulses.

Signal $V_{OUT}$ also is passed through analog-to-digital converter 193 and the digital output is fed to the microprocessor 180, where signal processing is performed to detect perturbations of the shape of the feedback signal that would indicate a blockage of the rotor of the stepper motor. Microprocessor 180 stops counting any detected motor pulses when it detects that the actuator is blocked, and outputs an indication of this status. Level detector 194 produces an output when it detects that the demodulated signal $V_{OUT}$ indicates the presence of the reference position signal $S_{RP}$ due to activation of the reference position switch. This output induces a reset of the position of the tension element calculated by microprocessor 180 in the external control. In this way, a small imprecision, e.g. an offset, can be corrected.

As described above, external control 16 may be configured to transmit both energy and commands to the implantable controller circuitry in antenna/controller pod 15. External control 16 may also receive feedback information from the implantable controller that can be correlated to the position of the tension element and the diameter of the loop. As will be apparent to one of skill in the art, external control 16 and the implantable controller may be configured in a master-slave arrangement, in which the implantable controller is completely passive, awaiting both instructions and power from external control 16.

Power may be delivered to the implantable pod 15 via magnetic induction. The quality of the coupling may be evaluated by analyzing the level of the feedback signal received by external control 16, and a metric corresponding to this parameter may be displayed on signal strength indicator 217 on control 16, which in the shown embodiment, includes 6 LEDs (corresponding to six levels of coupling). If the coupling between the antennae is insufficient, the motor of actuator may not work properly.

Figure 21:
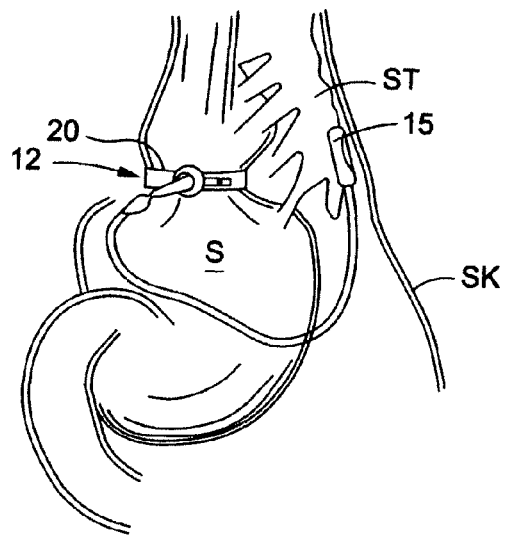
FIG. 21 is a schematic diagram illustrating placement of the implantable portions of the system of the invention.

Referring now to FIG. 21, band 20 of the presently described system of the invention is shown implanted in a patient. Band 20 of band 12 is disposed encircling the upper portion of the patient's stomach S while antenna/controller pod 15 is disposed adjacent to the patient's sternum ST. Pod 15 is located in this position beneath the patient's skin SK so that it is easily accessible in the patient's chest area to facilitate coupling of the implanted pod 15 to an external antenna of control 16.

Referring to FIGS. 22A to 22H, a method of implanting the band and pod of the system of the present invention is described. The method is similar to laparoscopic procedures used to implant previously-known hydraulically-actuated gastric bands.

Figures 22A, 22B, 22C, 22D, 22E, 22F, 22G, 22H:
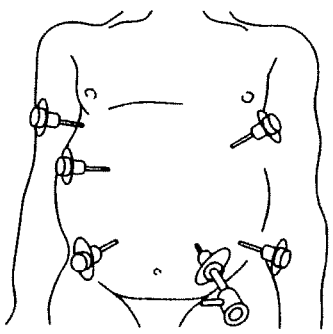

Access to the abdomen is obtained by using 4 to 6 small holes, generally 10 to 18 mm in diameter, with a trocar inserted in each hole, as depicted in FIG. 22A. A camera and laparoscopic surgical tools are introduced and manipulated through the trocars. In addition, to permit free motion of the surgical tools and camera, the abdomen is inflated with $CO_2$ to an overpressure of approximately 0.15 bars.

In FIGS. 22B-22E, the band 20 of the adjustable portion 12 is straightened (as depicted in FIG. 10) and inserted, antenna first, into the abdomen through an 18 mm trocar. Alternatively, a laparoscopic cannula may be used to make an incision and then withdrawn, and the device inserted through the opening so created (other instruments also may be used to form this laparotomy). In FIG. 22B, tag 18 of antenna/controller pod 15 is shown entering the abdomen through trocar 300 using atraumatic graspers 310. In FIG. 22C, housing 155 is shown being drawn into the abdomen through trocar 300, again using atraumatic graspers 310. FIG. 22D shows band 20 entering the abdomen in an extended position. In FIG. 22E, the band 20 is permitted to resume its arcuate shape.

Band 20 then is manipulated using atraumatic graspers 310 as described elsewhere herein, to secure the band 20 around the upper portion of the patient's stomach until slot 173 of clip 30 is engaged with flange 174, as shown in FIG. 22F. A fold of stomach tissue then may be sutured around the band 20 to prevent migration of the band 20.

Finally, as shown in FIG. 22G, a channel may be formed through the abdominal wall and antenna/controller pod 15 passed through the channel. Tag 18 then is cut off of antenna/controller pod 15, and the pod 15 is sutured into position above the patient's sternum, as depicted in FIG. 22H. The trocars then are removed, and the band 20 may be activated to adjust the diameter of the inner diameter as desired by the physician.

The process of removing the band 20 of the present invention involves substantially reversing the sequence of steps described above, and may be accomplished non-destructively. In particular, a plurality of cannulae into the abdominal cavity and the abdominal cavity then insufflated to create a pneumoperitoneum. Using laparoscopic graspers, the clip 30 may be unclipped and the band 20 removed from a position encircling the patient's stomach. The band 20 may then be straightened and withdrawn from the abdominal cavity either through one of the plurality of cannulae or via a laparotomy.

FIGS. 23 through 25 illustrate an alternative contact region 1010 of a gastric banding system of the present invention.

Contact region 1010 may be identical to contact region 44 except as explicitly described below. Contact region 1010 can replace contact region 44 described and shown, for example, in FIGS. 3 and 3A, in system 10.

Contact region 1010 comprises a membrane 1014 which may be substantially identical to membrane 45 described and shown elsewhere herein. In this embodiment however, cushion segments 1016, which may be made of the same incompressible materials as cushion segments 60, are affixed to an external surface of the membrane 1014 and define at least a portion of the stomach-facing surface of the contact region 1010. The cushion segments 1016 may be individually molded to, or molded as a whole, directly to the membrane 1014 using conventional molding techniques, for example, conventional overmolding techniques.

In a specific embodiment, cushions 1016 are made of silicone elastomer having a hardness of 10 Shore A and membrane 1014 is made of silicone elastomer having a hardness of 30 Shore A.

Alternatively, the membrane 1014 may be made of silicone elastomer of different hardness, such as, for example, 20 Shore A to 45 Shore A. Alternatively still, the cushions could be made of an even softer silicone elastomer, such as 5 Shore A or 1 Shore A. Alternatively, the cushions or the membrane could be made of other suitable implantable materials.

FIGS. 24 and 25 are cross sectional views of the contact region shown in FIG. 23 taken along line 24-24 and line 25-25, respectively.

Another feature of this embodiment of the invention is shown in FIG. 24. Specifically, the membrane 1014 may includes a structural support, for example, a wedge 1025 located at the interface between the membrane 1014 and each of the cushion segments 1016. Wedges 1025 may provide an increased surface area on which the cushion segments are molded thereby providing additional adherence and/or support between the membrane 1014 and the cushion segments 1016. Like membrane 45, membrane 1014 includes corrugations 1027 for facilitating unfolding or expansion of the membrane 1014 during adjustment of the band.

Figure 26:
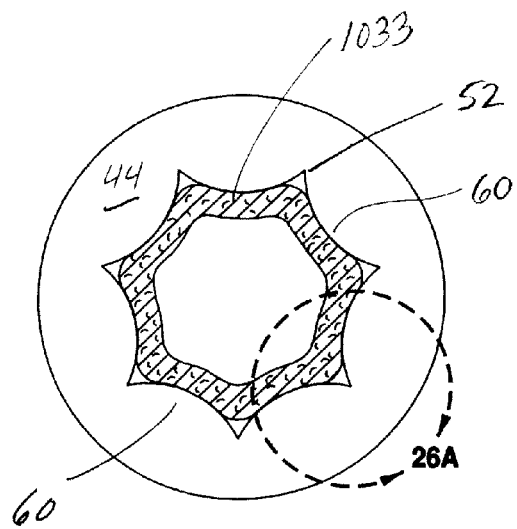
Figure 26A:
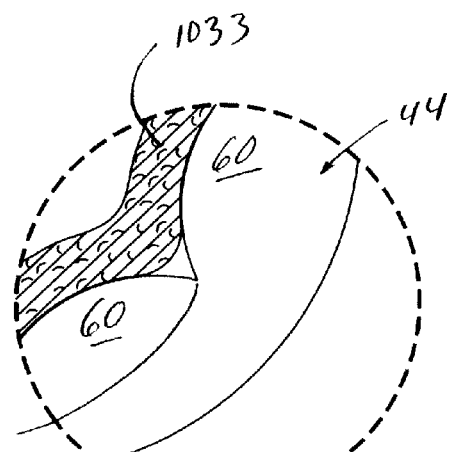
Figure 27:
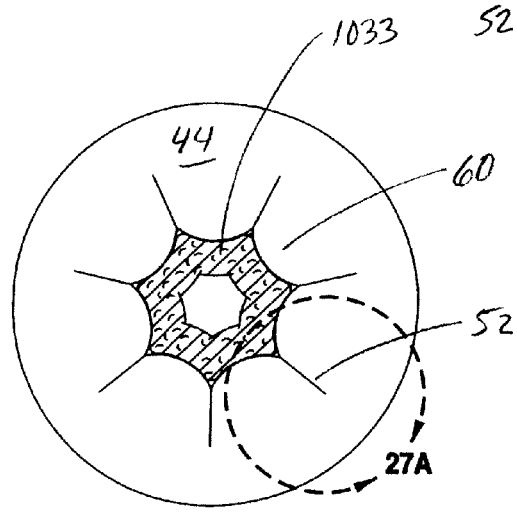
Figure 27A:
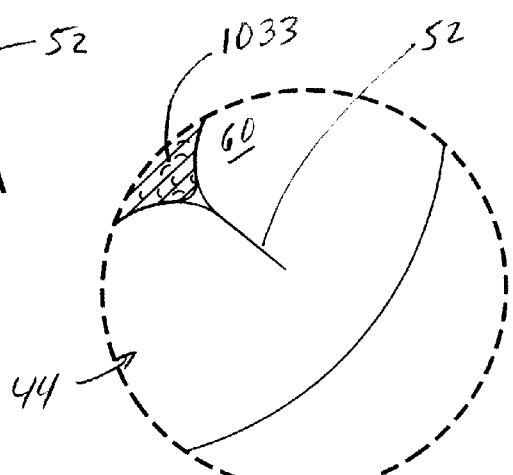

Another advantageous feature of this embodiment is shown in FIGS. 26-27A. In some embodiments, the cushion segments 60 and tension segments 52 form an inner circumference of the loop configuration having a generally star-shape, defined by the contact region, as shown in FIG. 26. The stomach lumen is indicated by numeral 1033. During constriction of the band, which is shown dilated in FIGS. 26 and 26A and constricted in FIGS. 27 and 27A, adjacent incompressible cushion segments 60 form, a progressively narrowing angle, for example, a progressively narrowing substantially V-shaped surface having convex, arcuate surfaces defined by the cushion segments 60. Tension segments 52 located between the adjacent cushion segments 60 and form the vertices of the angles.

While not wishing to be bound by any particular theory of operation, it is believed that the structure of the contact member 44 and at least partially due to the incompressibility of the cushion segments 60 enables the band to constrict about the stomach without pinching the tissue. For example, as shown in FIGS. 27 and 27A, the stomach tissue does not become entrapped between adjacent cushion segments 60. During constriction of the band, the convex stomach-facing surfaces maintain their shape and form no gaps, while folding inwardly toward one another. This mechanism and structure causes the tissues of the stomach constricted without the tissues becoming entrapped and/or pinched. This progressive V-shape acts differently than a mechanical pliers.

As stated elsewhere herein, the system of the present invention has numerous applications apart from gastric banding. For example, the system of the present invention may be used for the treatment of fecal incontinence, ileostomy, colostomy, gastro-esophageal reflux disease, urinary incontinence and isolated-organ perfusion.

For treatment of fecal incontinence, the ring may be used with little or no modifications. In addition, because the ring adjustment procedure will be performed by the patient on at least a daily basis, a portable user-friendly external control may be used. In addition, because the ring will regularly be transitioned between the closed and fully opened position, the patient microchip card is unneeded. Instead, the fully closed position may be stored in the memory of the implantable controller, and read by the external remote at each use (subject to periodic change by the physician).

A similarly modified device could be used by patients who have undergone ileostomy or colostomy, or disposed surrounding the esophageal junction, to treat gastro-esophageal reflux disease.

For treatment of urinary incontinence, the system of the present invention may be further modified to minimize the volume of the loop surrounding the urethra by moving the actuator motor to a location elsewhere in the lower abdomen or pelvis, and coupling the actuator to the motor via a transmission cable.

The present invention also may be beneficially employed to perform isolated-organ perfusion. The treatment of certain cancers requires exposure to levels of chemotherapy agents that are too high for systemic circulation. It has been suggested that one solution to this problem is perform an open surgery procedure in which blood flow to the cancerous organ is stopped and quiescent blood replaced by circulation from an external source containing a desired dose of drug. Individual or multiple rings of the present invention may be used as valves to isolate the cancerous organ and permit perfusion of the organ with high doses of drugs. Such procedures could thus be performed on a repetitive basis without surgery, thereby reducing the trauma and the risk to the patient while improving patient outcomes.

Although particular embodiments of the present invention have been described above in detail, it will be understood that this description is merely for purposes of illustration. Further variations will be apparent to one skilled in the art in light of this disclosure and are intended to fall within the scope of the appended claims.

What is claimed is:

1. A system for constricting a stomach of a patient for treating obesity, the system comprising:
    a gastric band having a first end, a second end, a distal region and a proximal region and a connector configured to couple the first end with the second end such that the gastric band is formable into a loop to circumscribe the stomach;
    a membrane disposed between the first end and the second end of the gastric band;
    at least one cushion segment coupled to the membrane and disposed on the proximal region of the gastric band; and
    a mechanism for enabling adjustment of an inner circumference of the loop, the mechanism comprising an interface connected to the gastric band, and a control capable of communicating with the interface to regulate constriction of the gastric band about the stomach;
    wherein the membrane includes at least one support wedge secured to the at least one cushion segment.

2. The system of claim 1 wherein the at least one cushion segment comprises a plurality of cushion segments disposed on the proximal region.

3. The system of claim 2 wherein the membrane defines a plurality of tension segments disposed in a substantially alternating manner between adjacent cushion segments.

4. The system of claim 1 wherein the at least one cushion segment is made of a substantially incompressible material.

5. The system of claim 1 wherein the at least one cushion segment is made of an incompressible material.

6. The system of claim 1 wherein the at least one cushion segment comprises a single incompressible cushion segment disposed along substantially the entire proximal region.

7. The system of claim 6 wherein the single incompressible cushion segment includes thick regions and relatively thin regions disposed in a substantially alternating manner between the thick regions.

8. The system of claim 1 wherein the at least one cushion segment is located on an external surface of the membrane.

9. The system of claim 1 wherein the at least one cushion segment is molded to the membrane.

10. The system of claim 1 wherein the at least one cushion segment is molded to an external surface of the membrane.

11. The system of claim 1 wherein the at least one cushion segment defines at least a portion of an inner circumferential surface of the gastric band when the gastric band is formed in the shape of the loop.

12. The system of claim 1 wherein the at least one cushion segment is substantially incompressible.

13. The system of claim 1 wherein the membrane includes corrugated surfaces to allow unfolding of the membrane during adjustment.

14. The system of claim 1 wherein the membrane is made of a first material and the at least one cushion segment is made of a second material having a different durometer than the first material.

15. The system of claim 1 wherein the at least one cushion segment is located on an internal surface of the membrane.

16. A system for constricting a stomach of a patient for treating obesity, the system comprising:
  a gastric band having a first end, a second end, a distal region and a proximal region and a connector configured to couple the first end with the second end such that the gastric band is formable into a loop to circumscribe the stomach;
  a contact region disposed between the first end and the second end of the gastric band, an inner circumference of the loop having a generally star-shape defined by the contact region; and
  a mechanism for enabling adjustment of the inner circumference of the loop;
  wherein the contact region includes a membrane and at least one cushion segment, the membrane disposed between the first end and the second end of the gastric band, and the at least one cushion segment coupled to the membrane and disposed on the proximal region of the gastric band, the membrane including at least one support wedge secured to the at least one cushion segment.

17. The system of claim 16 wherein the contact region includes a plurality of cushion segments spaced apart by a plurality of tension segments.

18. The system of claim 17 wherein the plurality of tension segments define vertices of the generally star-shape.

19. The system of claim 16 wherein the contact region is structured to prevent pinching of the organ when the gastric band is positioned around the stomach and the inner circumference is adjusted.

20. The system of claim 1 wherein the at least one cushion segment forms a substantially V-shaped surface.

21. The system of claim 1 wherein the at least one cushion segment comprises a plurality of cushion segments including a first segment defined by a convex stomach-facing surface and a second segment defined by a concave stomach-facing surface.

* * * * *